(12) United States Patent
McCarvill et al.

(10) Patent No.: US 8,092,550 B2
(45) Date of Patent: Jan. 10, 2012

(54) LOWER LEG PROSTHESIS WITH IMPROVED ROLL OVER

(75) Inventors: Sarah McCarvill, Salt Lake City, UT (US); David J. Wall, Sandy, UT (US); Eric W. Rubie, Salt Lake City, UT (US); Bret J. Geilman, North Ogden, UT (US); Nathan A. Williams, Goettingen (DE)

(73) Assignee: Otto Bock HealthCare LP, Minneapolis, MN (US)

( * ) Notice: Subject to any disclaimer, the term of this patent is extended or adjusted under 35 U.S.C. 154(b) by 1129 days.

(21) Appl. No.: 11/230,212

(22) Filed: Sep. 19, 2005

(65) Prior Publication Data

US 2006/0069450 A1  Mar. 30, 2006

Related U.S. Application Data

(60) Provisional application No. 60/610,733, filed on Sep. 18, 2004.

(51) Int. Cl.
*A61F 2/66* (2006.01)
(52) U.S. Cl. ........................................... 623/55
(58) Field of Classification Search .................. 623/52, 623/53, 55
See application file for complete search history.

(56) References Cited

U.S. PATENT DOCUMENTS

| | | | |
|---|---|---|---|
| 5,019,109 A | 5/1991 | Voisin | |
| 5,037,444 A | 8/1991 | Phillips | |
| 5,181,933 A | 1/1993 | Phillips | |
| 5,314,499 A * | 5/1994 | Collier, Jr. | 623/47 |
| 5,482,513 A * | 1/1996 | Wilson | 623/52 |
| 5,514,185 A | 5/1996 | Phillips | |
| 5,769,896 A | 6/1998 | Rosendahl et al. | |
| 5,776,205 A | 7/1998 | Phillips | |
| 5,800,569 A | 9/1998 | Phillips et al. | |
| 5,944,760 A | 8/1999 | Christensen | |
| 6,071,313 A | 6/2000 | Phillips | |
| 6,120,547 A | 9/2000 | Christensen | |

(Continued)

FOREIGN PATENT DOCUMENTS

DE  299 12 832  11/2000

(Continued)

OTHER PUBLICATIONS

International Search Report for PCT/US2005/033691, Jun. 27, 2006.

*Primary Examiner* — Bruce E Snow
*Assistant Examiner* — Melissa Hoban
(74) *Attorney, Agent, or Firm* — Holland & Hart

(57) ABSTRACT

A foot prosthesis having improved rollover and stability. The prosthesis includes a first plate and a mounting block having a mounting portion configured to be coupled to a user of the prosthesis, an attachment portion and a gap portion, with the mounting block attached to the first plate at the attachment portion with a gap between the mounting block gap portion and the first plate. Also included is a resilient element positioned at least partially within the gap, the resilient element configured generally to dissipate stress in the first plate and control deflection between the first plate and the mounting block. The mounting block may be substantially rigid with the area of the first plate attached to the mounting block becoming substantially rigid while the remainder of the first plate is at least partially flexible. The resilient element may be interchangeable to adjust performance of the prosthesis.

21 Claims, 30 Drawing Sheets

U.S. PATENT DOCUMENTS

| | | |
|---|---|---|
| 6,197,068 B1 | 3/2001 | Christensen |
| 6,241,776 B1 | 6/2001 | Christensen |
| 6,719,807 B2 * | 4/2004 | Harris ............... 623/55 |
| 2002/0013628 A1 * | 1/2002 | Harris ............... 623/55 |
| 2002/0077706 A1 * | 6/2002 | Phillips ............ 623/52 |
| 2002/0087216 A1 | 7/2002 | Atkinson et al. |
| 2002/0116072 A1 | 8/2002 | Rubie et al. |
| 2003/0045944 A1 * | 3/2003 | Mosler et al. ............ 623/52 |
| 2004/0068327 A1 * | 4/2004 | Christensen ............ 623/52 |
| 2005/0038525 A1 * | 2/2005 | Doddroe et al. ............ 623/55 |

FOREIGN PATENT DOCUMENTS

| | | |
|---|---|---|
| GB | 625 528 | 6/1949 |
| WO | WO2005027802 | 3/2005 |

* cited by examiner

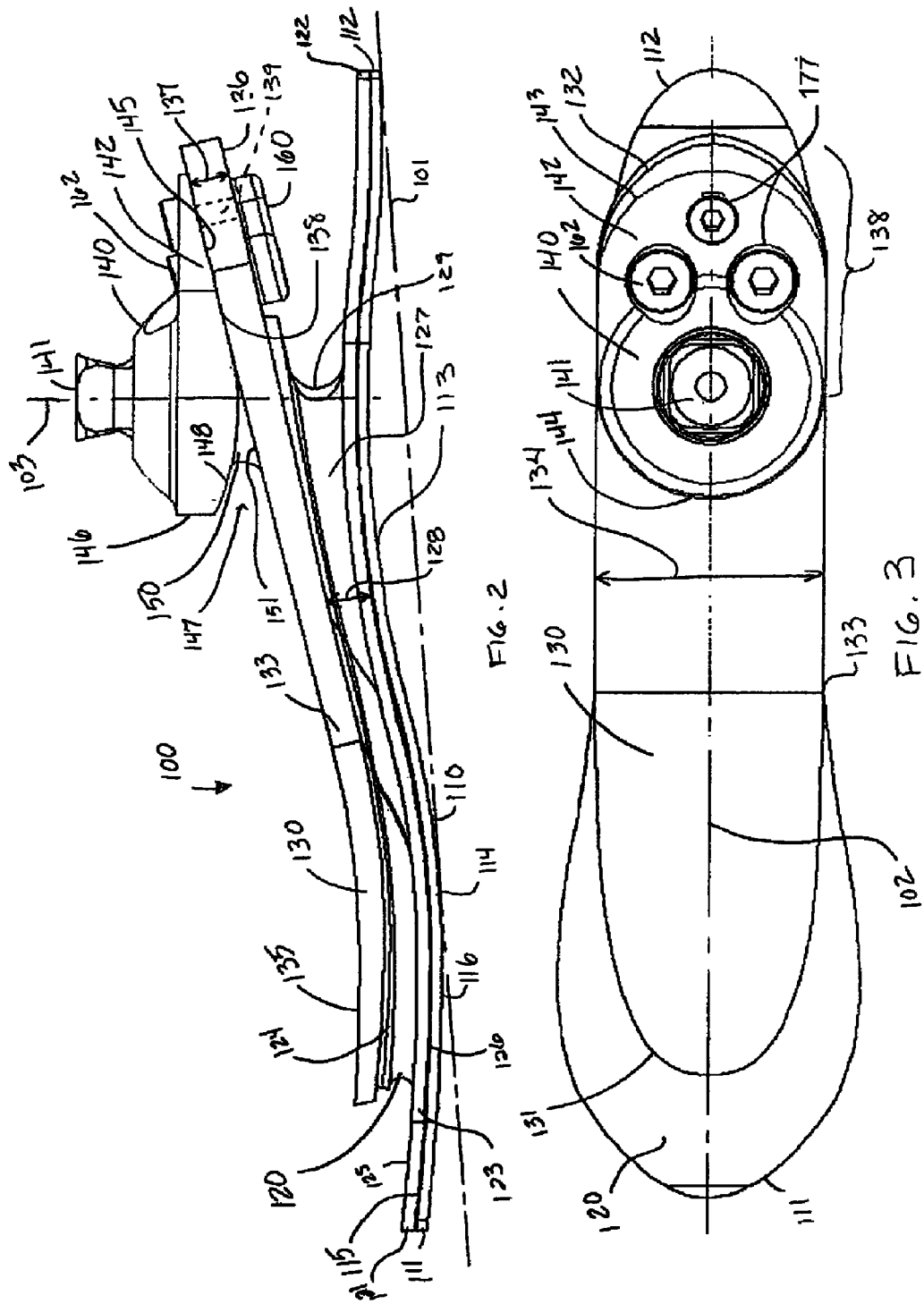

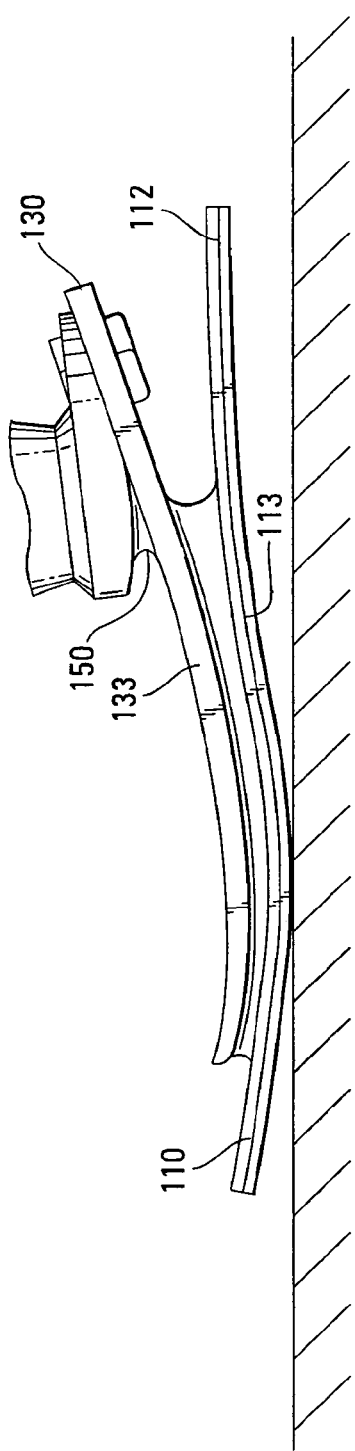
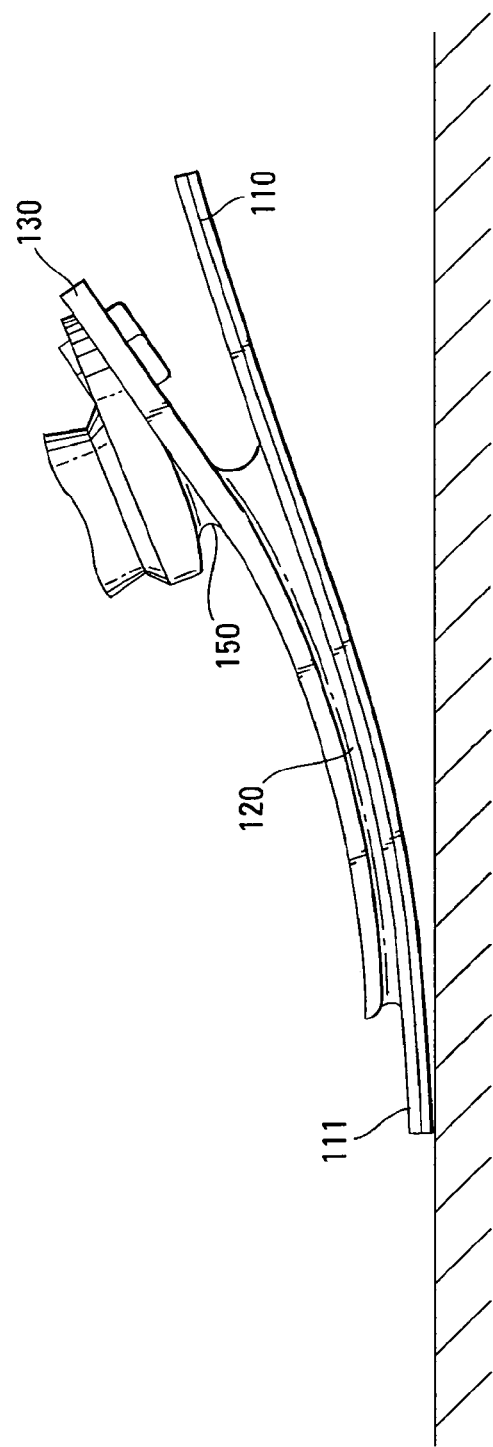

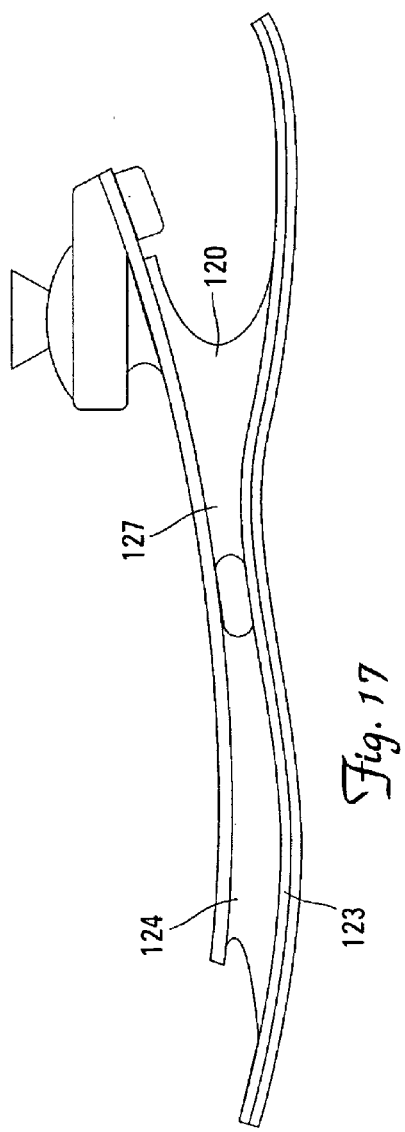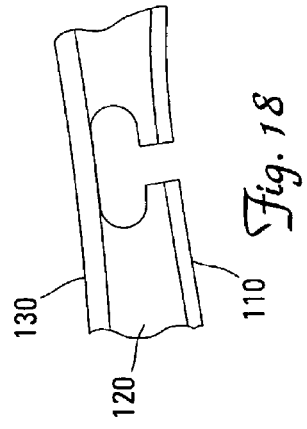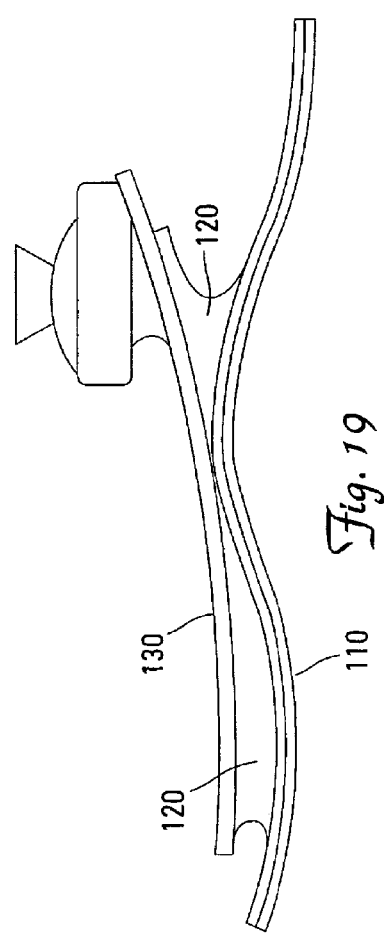

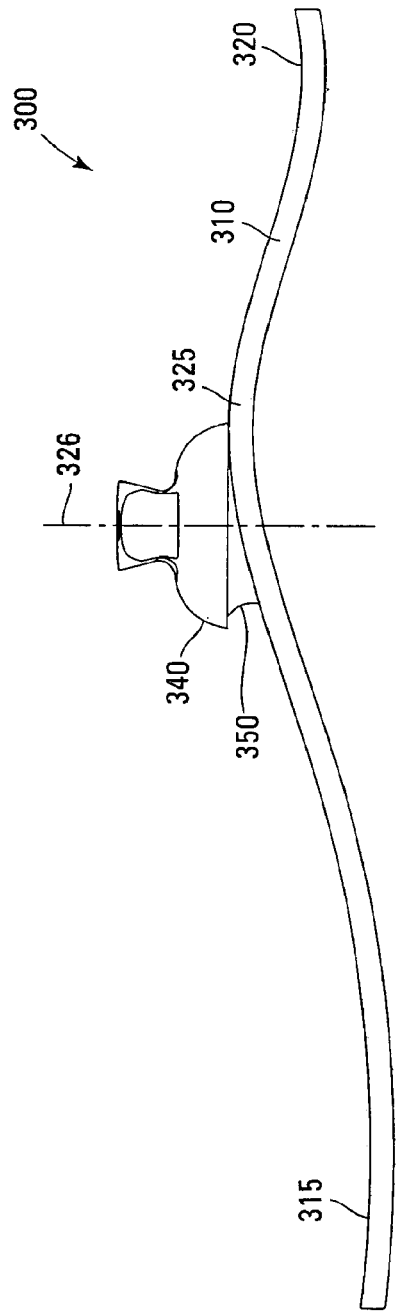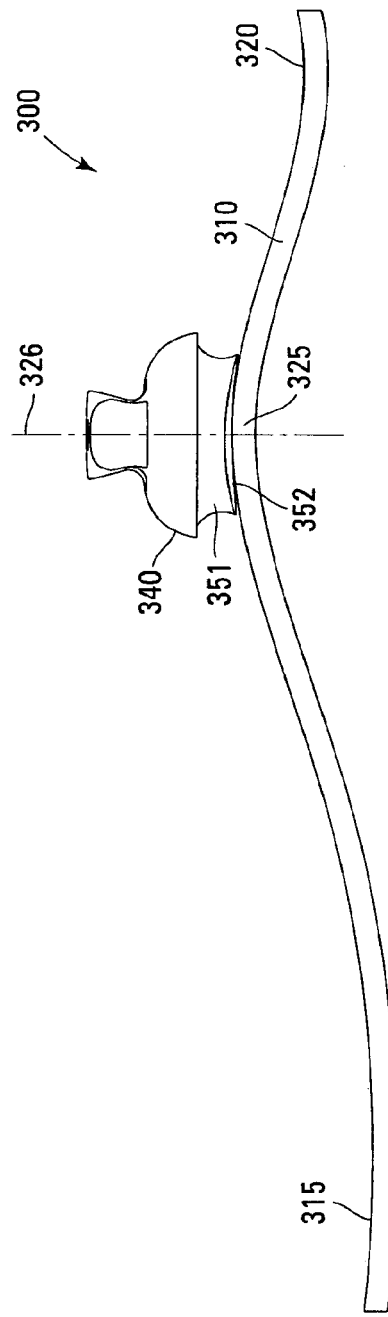

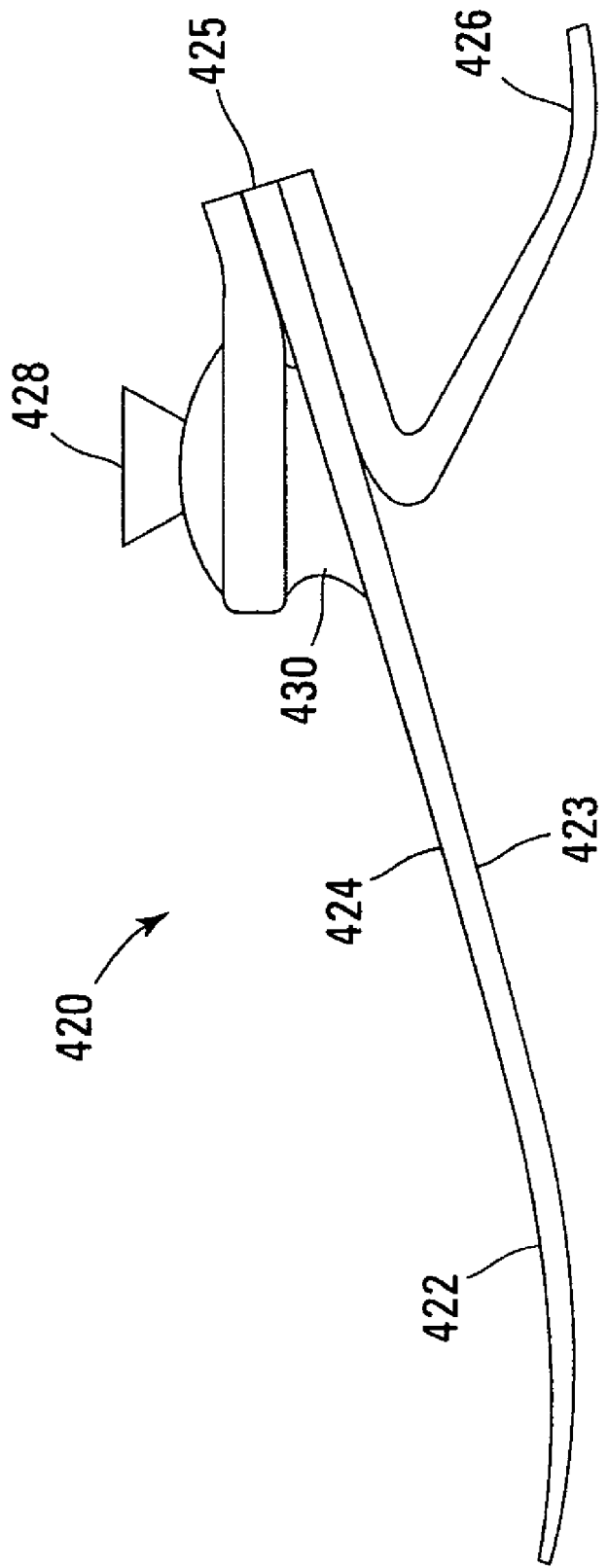

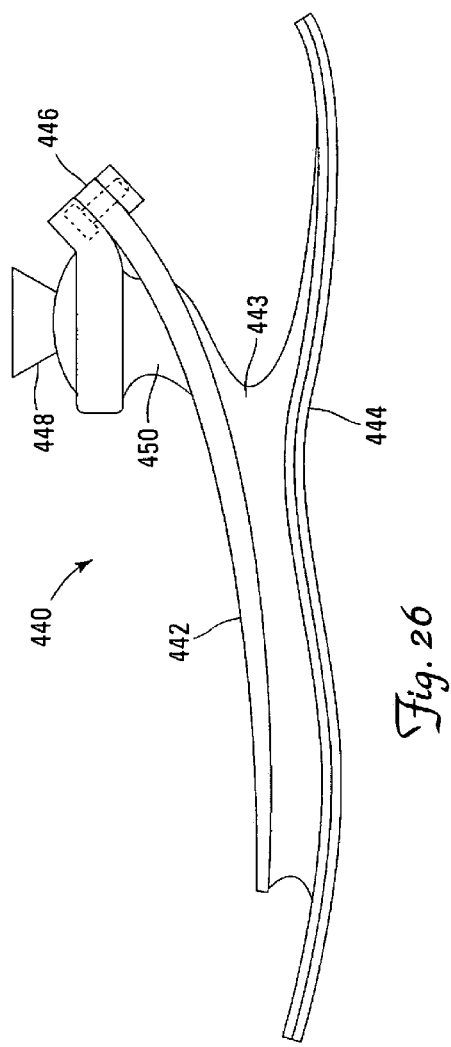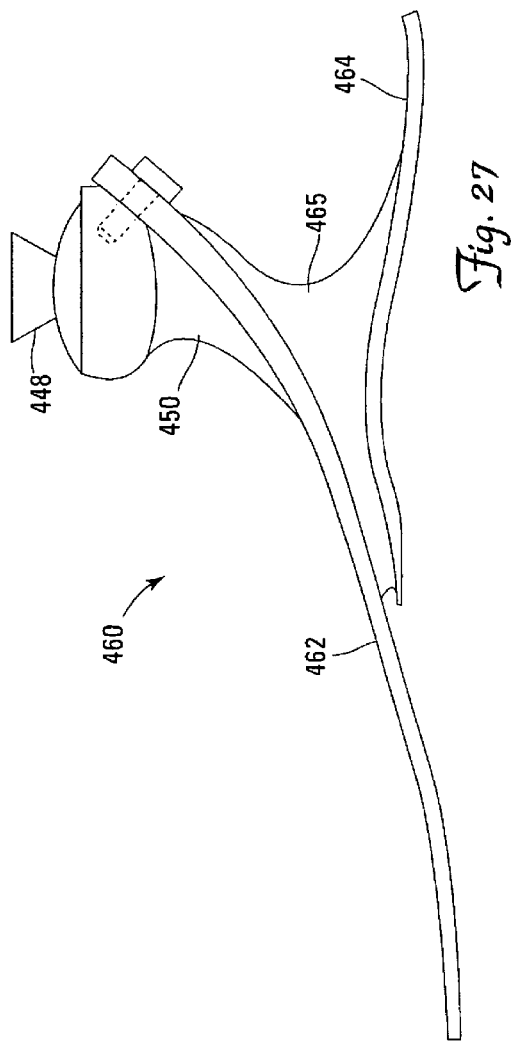

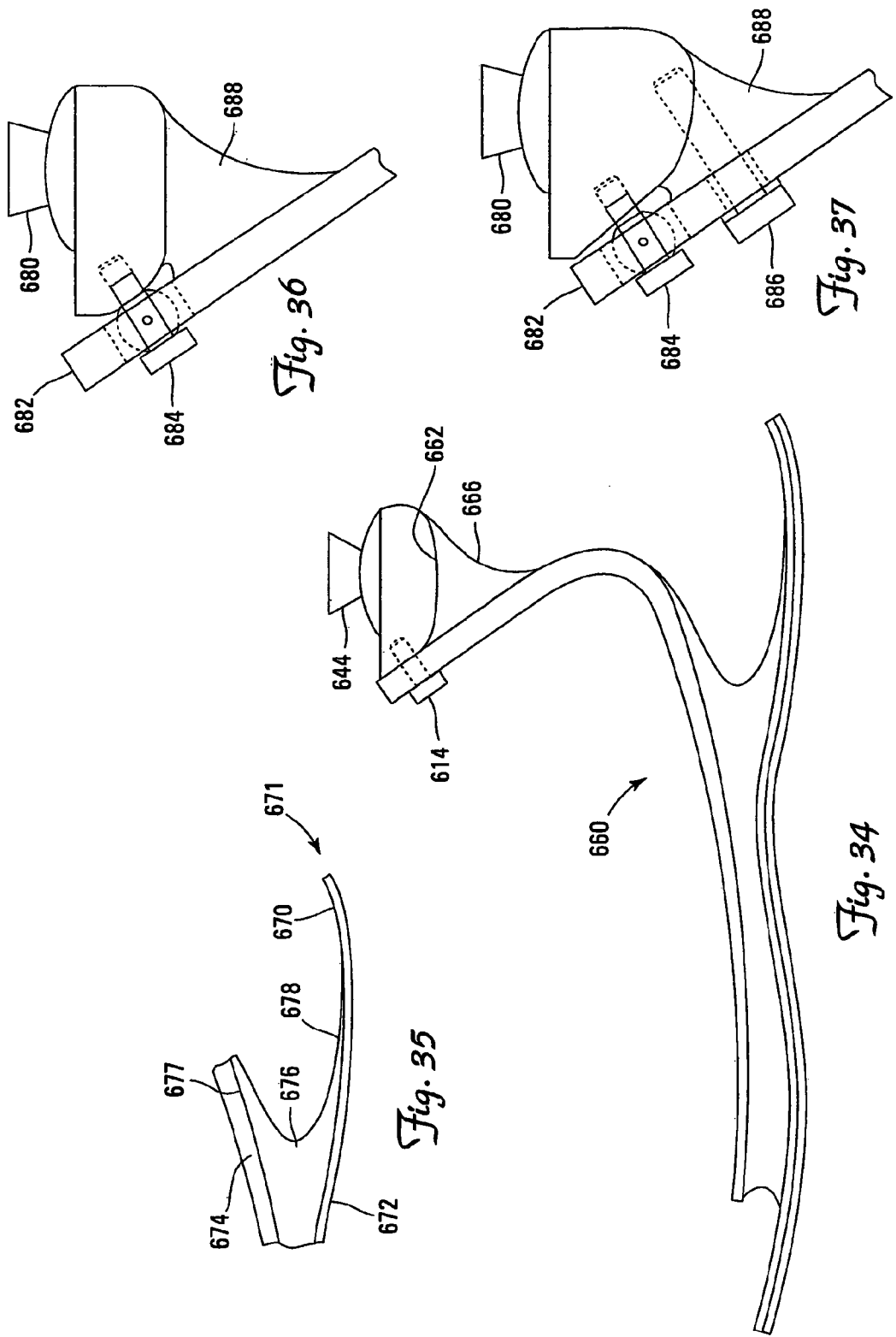

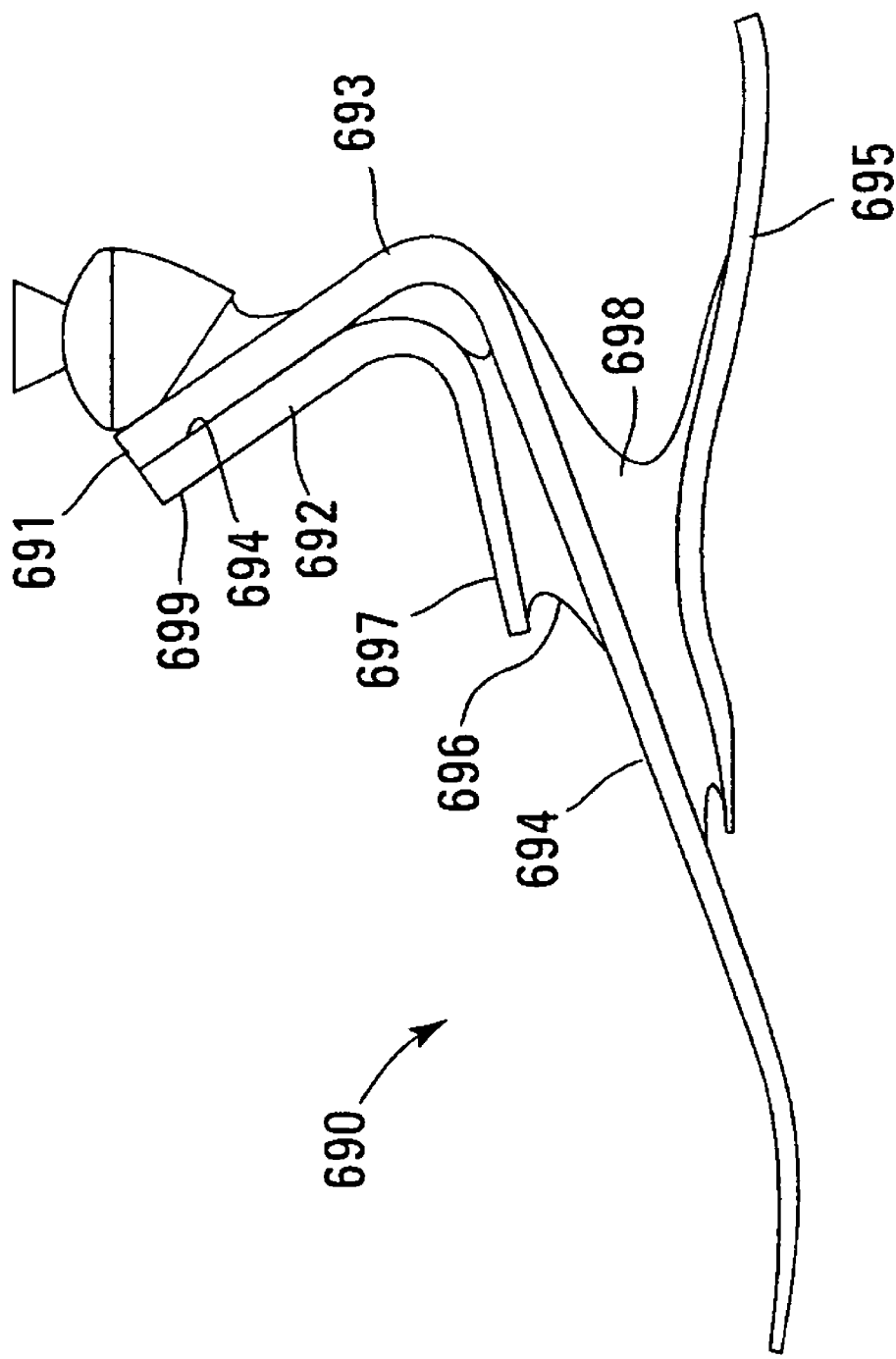

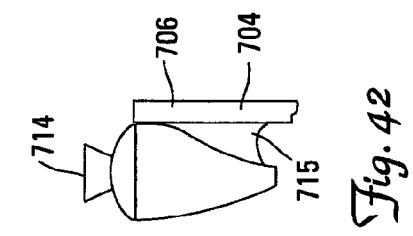
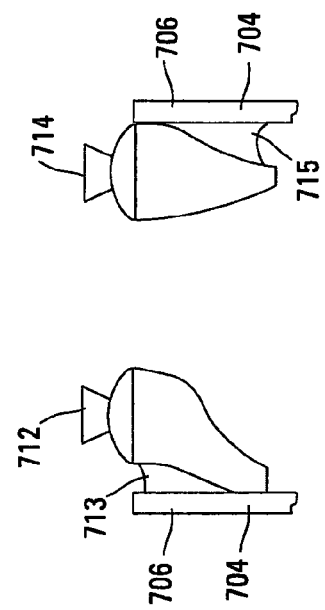
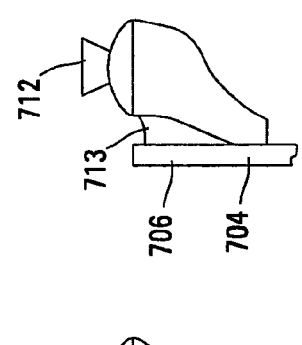
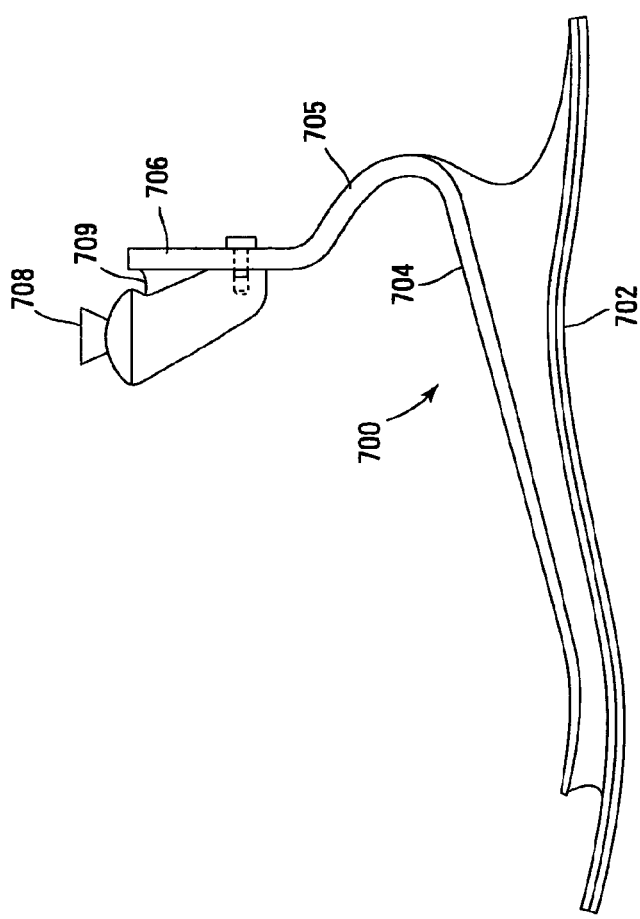

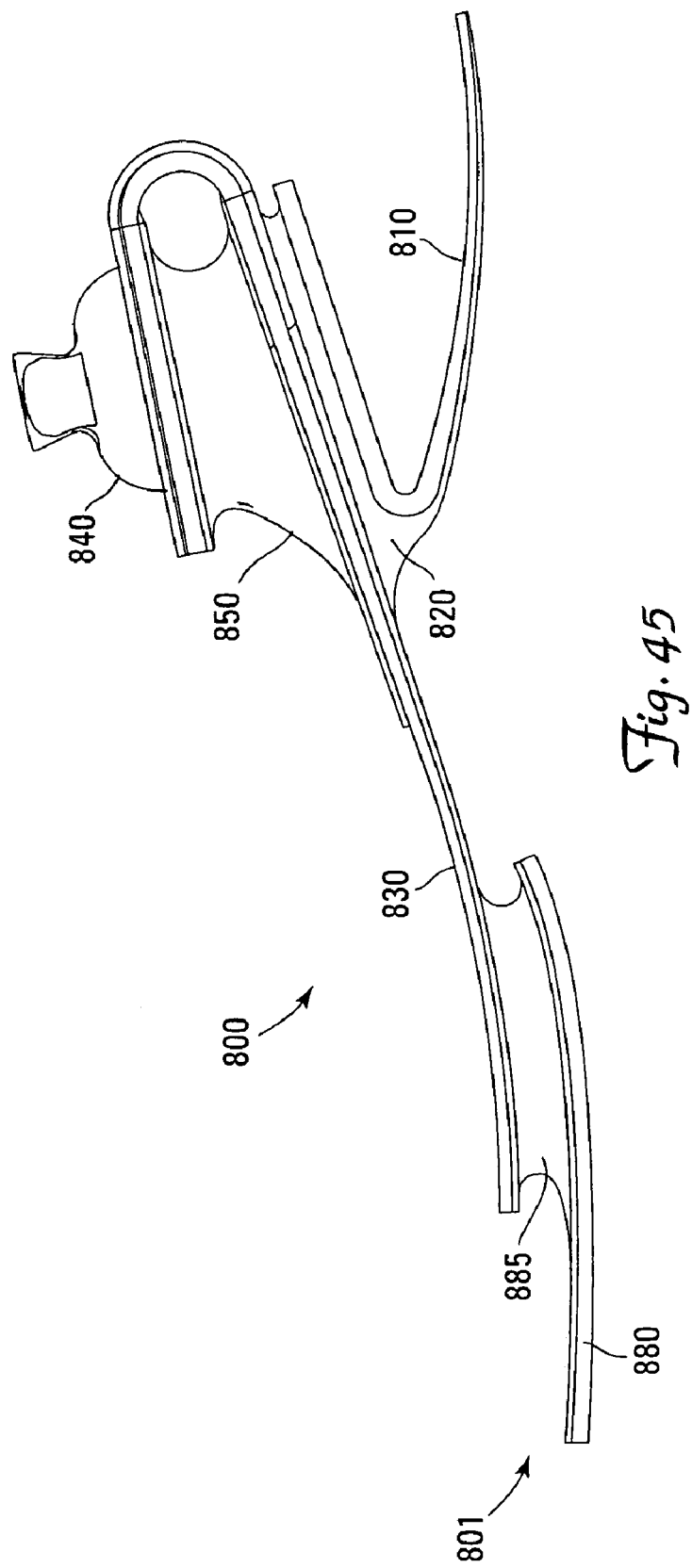

US 8,092,550 B2

LOWER LEG PROSTHESIS WITH IMPROVED ROLL OVER

This application claims the benefit of U.S. provisional patent application, Ser. No. 60/610,733, filed on Sep. 18, 2004, and herein incorporated by reference in its entirety.

FIELD OF THE INVENTION

This invention relates generally to lower leg prostheses and, more particularly, to lower leg prostheses configured to duplicate the performance characteristics of the natural human foot.

BACKGROUND OF THE INVENTION

Significant advancements in the field of lower leg prostheses have been made in recent years, due largely to the development of composite materials technology. Lower leg prostheses incorporating fiberglass/epoxy and carbon fiber/epoxy composite materials have been developed, which closely duplicate the performance characteristics and feel of the natural human foot and ankle.

One such lower leg prosthesis is sold by Otto Bock HealthCare, under the name Advantage Low Profile. That prosthesis incorporates a flexible lower member and a relatively rigid upper member, which are attached together by an intermediate elastomeric layer. A toe portion of the lower member projects beyond a forward end of the upper member, and a heel portion of the lower member projects beyond a rearward end of the upper member. The lower and upper members are formed of a high-strength, carbon fiber/epoxy composite material, and the intermediate layer is formed of a high-density polyurethane material. An attachment pyramid is mounted on the upper member, for attaching the lower leg prosthesis to a socket for receiving the amputee's residual limb or to an intermediate prosthetic component such as a pylon. A crepe or rubber sole can be attached to the underside of the lower member, and a foam foot shell or cosmesis can be placed over the members, to provide the prosthesis with an appearance of a natural human foot.

The Advantage Low Profile prosthesis described briefly above has enjoyed commercial success. Many other types of low profile lower leg prostheses are currently on the market, including the Otto Bock Luxon Max, Low Profile, and Luxon Journey. In addition, there are bssur's LP Vari-Flex® foot and Freedom Innovations' FS2000 LP (Low Profile) foot. Each of these lower profile foot prostheses has advantages and disadvantages. Nevertheless, it is believed that there is still a need for a foot prosthesis that provides greater stability during use, particularly at heel strike and at toe-off, and also provides greater smoothness throughout the transition from heel to toe, thus coming closer to duplicating the performance and feel of the natural human foot and ankle.

SUMMARY OF THE INVENTION

The present invention provides a foot prosthesis having improved rollover and stability. The foot prosthesis includes a first plate and a mounting block having a mounting portion configured to be coupled to a user of the foot prosthesis, an attachment portion and a gap portion, the mounting block is attached to the first plate at the attachment portion with a gap between the mounting block gap portion and the first plate. Also included is a resilient element positioned at least partially within the gap. In one embodiment, the resilient element is configured to dissipate stress in the first plate and control deflection between the first plate and the mounting block. In another embodiment, the mounting block is substantially rigid and the area of the first plate attached to the mounting block becomes substantially rigid while the remainder of the first plate is at least partially flexible. In yet another embodiment, the resilient element may be removable and interchangeable to adjust performance of the prosthesis.

BRIEF DESCRIPTION OF THE DRAWINGS

FIG. 2 is a side elevational view of the foot prosthesis of FIG. 1.

FIG. 3 is a top plan view of the foot prosthesis of FIG. 1.

FIGS. 11-14 are a series of side elevational views of the foot prosthesis of FIG. 1, showing the prosthesis in a sequence of stages of a normal step.

FIG. 17 is a side view of a foot prosthesis in accordance with the present invention including an opening in the intermediate layer.

FIG. 18 is a partial view of the foot prosthesis of FIG. 17 wherein the opening extends through the lower foot member.

FIG. 19 is a side view of a foot prosthesis in accordance with the present invention including an area in the intermediate layer of about zero thickness.

FIG. 22 is a side view of a foot prosthesis in accordance with the present invention formed from a single member with a resilient element positioned toward the toe.

FIG. 23 is a side view of the foot prosthesis of FIG. 22, wherein the resilient element extends toward the toe and the heel.

FIGS. 24-42 are side views, and partial side views, of various embodiments of a foot prosthesis in accordance with the present invention, including detailed views of the mounting block, resilient element and other components.

FIGS. 43-45 are side views of various embodiments of a foot prosthesis in accordance with the present invention including an upper member having a bend forming a gap into which a resilient element is positioned.

DETAILED DESCRIPTION OF PREFERRED EMBODIMENTS OF THE INVENTION

Figure 1:
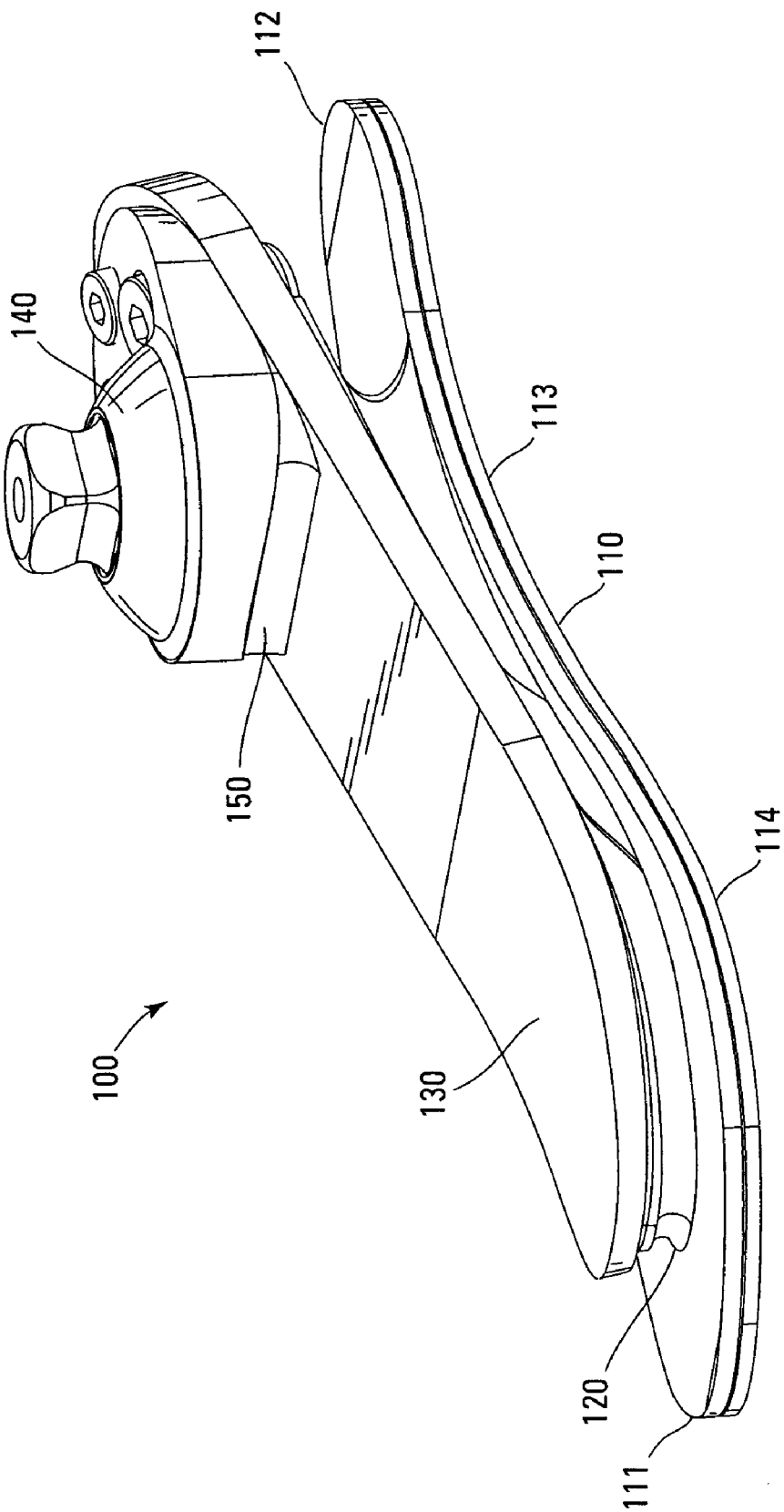
FIG. 1 is a perspective view of a foot prosthesis in accordance with one embodiment of the invention.

With reference to the attached Figures, it is to be understood that like components are labeled with like numerals throughout the several Figures. FIGS. 1-5 illustrate one embodiment of a foot prosthesis 100 in accordance with the present invention. The prosthesis 100 includes a lower foot member or plate 110 configured as having an elongated, substantially oval shape that is generally about the size of a human foot. Both a forward end 111, or toe portion, and a rearward end 112, or heel portion, of the foot member 110 are rounded so as to facilitate insertion and removal of the prosthesis 100 into a cosmesis. The prosthesis 100 and foot member 110 may be provided in various sizes to meet the needs of foot prosthesis users of different ages, body weights and foot sizes, and to accommodate the interior requirements of different sizes of foot cosmeses. In one embodiment, the shape of the lower foot member 110 is substantially symmetrical about a longitudinal axis 102, such that the prosthesis 100 may be used as either a left or a right foot replacement. However, it is also possible to shape the lower foot member 110 so as to be specifically for a right or a left foot.

Figure 5:
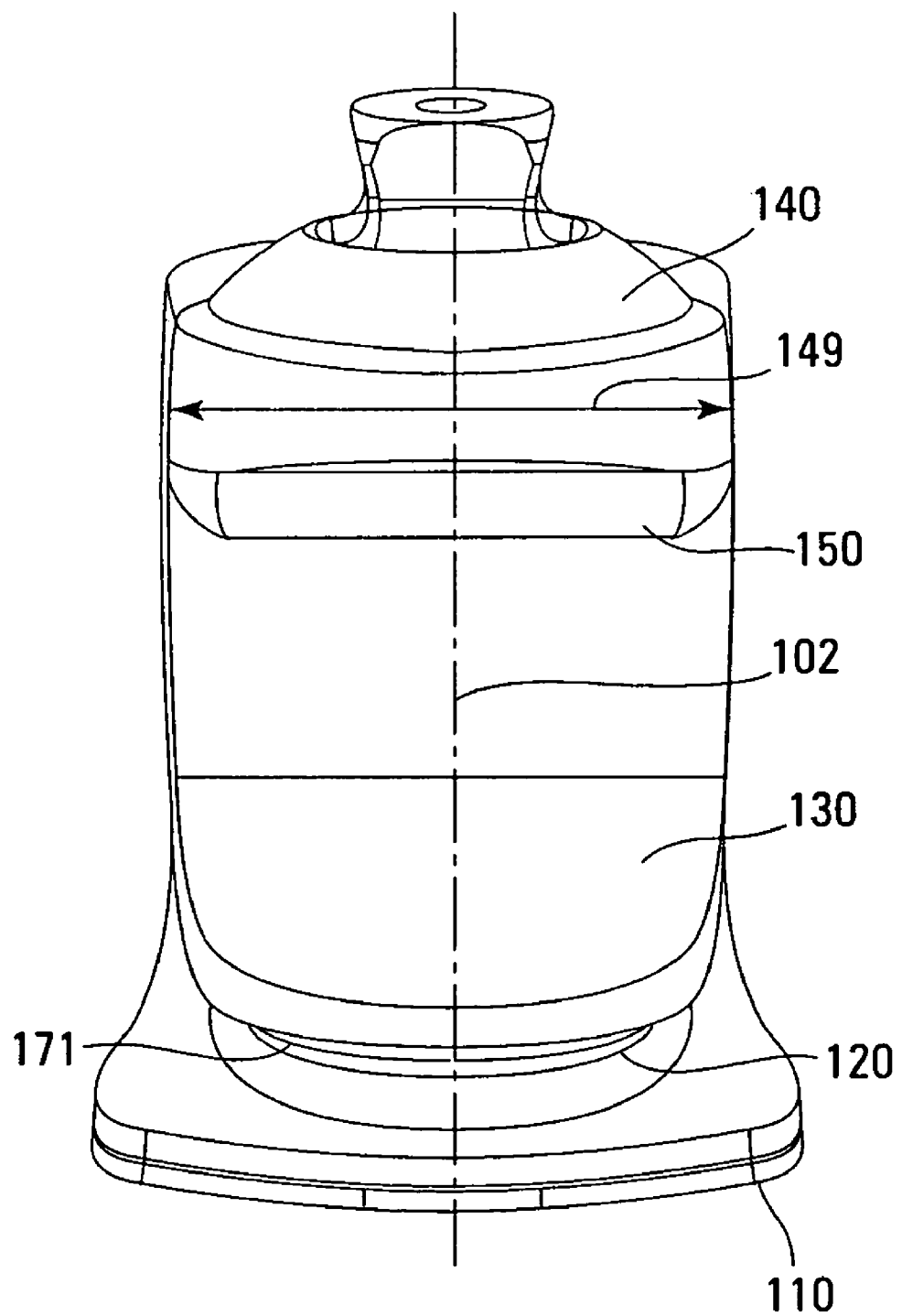
FIG. 5 is a front elevational view of the foot prosthesis of FIG. 1.

The lower foot member 110 includes an upper surface 115 and a lower surface 116, with the lower surface 116 configured to engage an interior surface of a cosmesis or to function as a sole of the foot prosthesis 100. An additional layer of sole material, such as crepe, rubber or a similar resilient and/or higher friction material, may optionally be applied to the lower surface 116 to, for example, provide better traction when the prosthesis 100 is worn and used without a cosmesis or shoe. The upper surface 115 is generally flat transversely across the lower foot member 110, as seen in FIG. 5.

Figure 7:
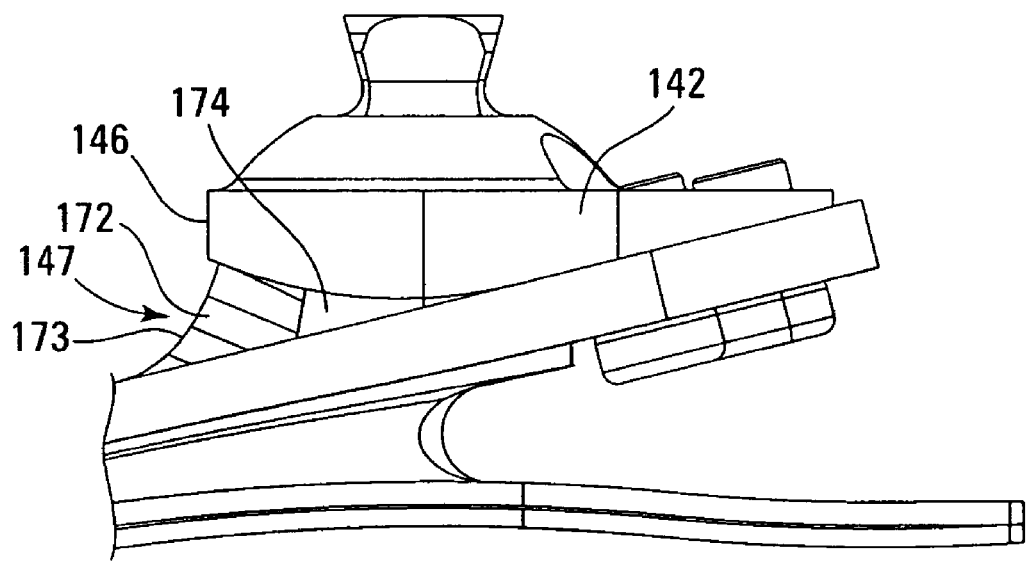
FIG. 7 is a partial side view of the foot prosthesis in accordance with the present invention showing an alternative embodiment of a resilient element.

The lower foot member 110 has a generally curvilinear cross-section from the toe portion 111 to the heel portion 112, as seen in FIGS. 2 and 7. The forward toe portion 111 curves upward, away from a theoretical plane 101 upon which the prosthesis 100 may rest. A ball portion 114 and the rearward heel portion 112 are curved downward so as to contact the plane 101. A mid-arch portion 113 curves upward, away from the plane 101, in a manner similar to the natural arch of a human foot. The lower foot member 110 is generally uniform in thickness from the toe portion 111 to the heel portion 112. In one embodiment, the thickness is about 0.12 inch (about 3 millimeters), but may vary in thickness from about 0.058 inch to about 0.15 inch (about 1.5 millimeters to about 3.8 millimeters) to accommodate varying body weights and activity levels of the user. In another embodiment, the heel portion 112 of the lower foot member 110 may be slightly thicker than the toe portion 111. In one embodiment, the difference between the thicknesses may range from none (as with the prior embodiment) to about 0.1 inch (about 2.5 millimeters). In another embodiment, the difference may be about 0.012 inch (about 0.3 millimeters).

The prosthesis 100 also includes an upper member or plate 130 that is configured generally as an elongated oval and is generally shorter in length than the lower foot member 110. The upper member 130 is positioned above and spaced apart from the upper surface 115 of the lower foot member 110. The upper member 130 also may vary in size, depending on the desired size of the foot prosthesis 100. In one embodiment, the upper member 130 is provided in two different lengths depending on the length range of the lower foot member 110. In one embodiment, a foot prosthesis size range of about 10.2 inches to about 12.0 inches (about 26 to about 31 centimeters) will use an upper member with a length of about 7.5 inches (about 19 centimeters), such as that shown in FIGS. 1-3. A foot prosthesis size range of about 8.6 inches up to about 10.3 inches (about 22 up to about 26 centimeters) will use an upper member with a length of about 6.4 inches (about 16.3 centimeters), such as that shown in FIG. 10 and described more below. In another embodiment, the upper member 130 is incrementally sized depending on the length of the lower foot member 110.

The upper member 130 has a curved forward or toe portion 131 and a curved rearward or heel portion 132, similar to the lower foot member 110, as seen in FIG. 3. These curved end portions 131, 132 also help facilitate insertion of the prosthesis 100 into and removal from a cosmesis. The upper member 130 has a width 134 that is substantially constant from the curved heel portion 132 forward to the start of the curved toe portion 131 at about a mid location 133. In one embodiment, the width 134 is generally the same as a width of the lower foot member 110, as shown in FIG. 3. Alternatively, the width 134 may be narrower than the lower foot member 110. It has been found through testing that the constant width configuration of the present invention generally provides a more durable design than those including shape changes in the rear portion of the upper member.

The upper member 130 also includes an upper surface 135 and a lower surface 136, with the lower surface 136 facing the upper surface 115 of the lower foot member 110. The upper surface 135 is generally flat transversely across the width 134 and may include a decorative layer or treatment for aesthetic and/or marketing purposes.

The upper member 130 is generally straight from the heel portion 132 forward toward about the mid location 133 and is curved from about the mid location 133 forward to through the toe portion 131. The toe portion 131 is curved upwardly, away from the lower foot member 110 in a configuration similar to the toe portion 111 of the lower foot member 110. The upper member 130 includes a thickness 137 that is substantially constant in the heel portion 132 forward through a mounting region 138, and then can decrease forward to the toe portion 131. The thickness at the heel portion 132 may vary from about 0.2 inch to about 0.4 inch (about 5 millimeters to about 10 millimeters), or more preferably from about 0.25 inch to about 0.31 inch (about 6.2 millimeters to about 7.9 millimeters). The thickness in the toe portion 131 may vary from about 0.05 inch to about 0.2 inch (about 1.2 millimeters to about 5 millimeters), or more preferably from about 0.09 inch to about 0.15 inch (about 2.3 millimeters to about 3.8 millimeters). In one embodiment, the thickness is about 0.28 inch (about 7 millimeters) in the mounting region 138 and tapers to a thickness of about 0.12 inch (about 3 millimeters) at the toe portion 131.

The lower foot member 110 and the upper member 130 are both preferably formed of a conventional epoxy/carbon fiber composite material, like the material used in known commercial products, such as Otto Bock's Luxon Max prosthetic foot. However, other suitable materials may also be used, as are now known or later developed in the art.

The foot prosthesis 100 also includes an intermediate layer or member 120 interposed between the lower foot member 110 and the upper member 130. The intermediate layer 120 serves as a cushioning means between the lower foot member 110 and upper member 130. In one embodiment, the intermediate layer 120 is formed from non-foam polyurethane, however, other elastomeric, resilient and/or compressible materials may also be used. These may include, but are not limited to, polymer foam, silicone rubber, butyl rubber, and natural rubber, all of which may be provided in different durometers that provide different degrees of compressibility, elasticity, etc., depending on the requirements of the prosthesis and the user. The intermediate layer 120 can, for example, be made from the same material that is used between the upper foot, lower foot and heel portions of Otto Bock's existing Luxon Max prosthetic foot.

The intermediate layer 120 includes an lower portion 123 formed generally to conform to the size and shape of the lower foot member 110, including a curved toe portion 121 and a curved heel portion 122. The intermediate layer 120 also includes an upper portion 124 sized and shaped to conform generally to the upper member 130, except shorter in length near the heel portion 132. In one embodiment, the upper section 124 is the same width 134 as the upper member 130. Alternatively, the upper portion 124 is slightly smaller than the width 134 to facilitate the assembly process. The intermediate layer 120 also includes an upper surface 125 that has multiple levels as it extends over the lower portion 123 and the upper portion 124.

The intermediate layer 120 further includes a middle portion 127 interposed between the upper portion 124 and the lower portion 123. The intermediate layer 120 has a thickness 128 through the middle portion 127, which may vary from a rear side 129 toward the toe portion 121. In one embodiment, the thickness 128 near the rear side 129 may be about 0.3 inch to about 0.7 inch (about 7.6 millimeters to about 17.8 millimeters) and toward the toe portion 122 the thickness 128 may be about 0.2 inch to about 0.6 inch (about 5.1 millimeters to about 15.2 millimeters). In between, the thickness 128 may be about zero inches to about 0.5 inch (about zero millimeters to about 12.7 millimeters), depending on the requirements for the user.

Figure 4:
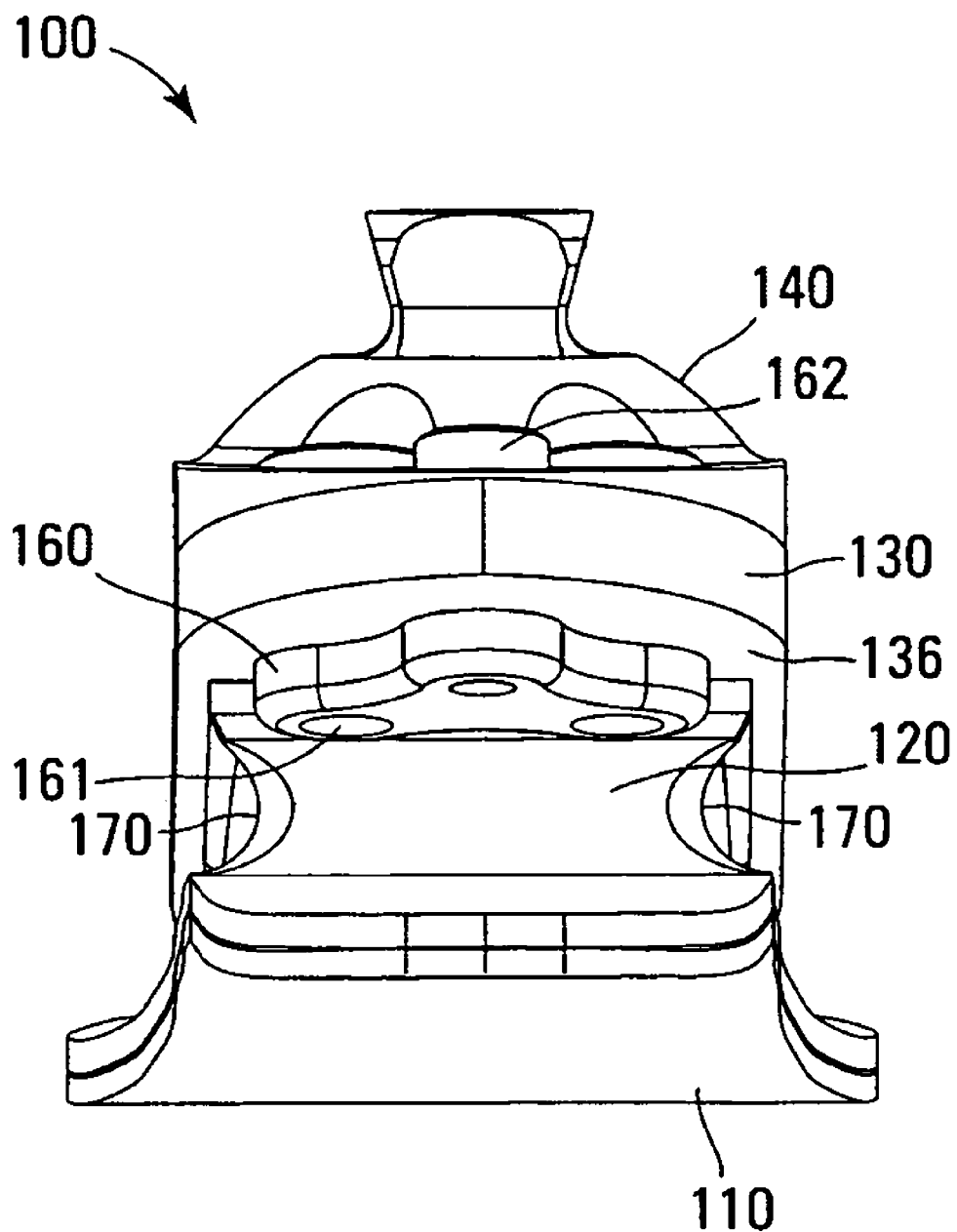
FIG. 4 is a back elevational view of the foot prosthesis of FIG. 1.

The middle portion 127 extends in length from about the toe portion 131 of the upper member 130 to near a rear end of the upper portion 124. The middle portion 127 has concave sides 170, as shown in FIG. 4, which extend around a curved toe portion 171, as shown in FIG. 5.

The rear side 129 of the middle portion 127 is generally formed as a concavity that extends transversely across a width of the middle portion 127. In one embodiment, the rear side 129 is a generally full radius. Alternatively, the rear side 129 concavity may be generally elliptical, square, rectangular, angular or other shape, found to provide the required performance. The size of the radius or other concavity can vary depending on the thickness 128 at the rear side 129. Although shown with the rear side 129 concavity aligned with the centerline 103 of the mounting unit 140, the rear side 129 may be positioned forward or rearward of the centerline 103 as desired to achieve performance requirements.

In one embodiment, the lower portion 123 of the intermediate layer 120 extends over substantially the whole upper surface 115 of the lower foot member 110 with a lower surface 126 in contact with the upper surface 115 of the lower foot member 110. However, in other embodiments, the lower portion 123 extends over only part of the upper surface 115. In some embodiments, the lower portion 123 has a generally uniform thickness in areas that extend beyond the middle portion 127; in other embodiments, this thickness may vary. The thickness may be about 0.1 inch (about 2.5 millimeters), but may be smaller or larger, depending on the requirements of the prosthesis 100. In a similar manner, the upper portion 124 of the intermediate layer 120 may also extend beyond the middle portion 127 with a thickness in the range of about 0.1 inch (about 2.5 millimeters), but may also be smaller or larger depending on the requirements of the prosthesis 100.

When assembled, the lower foot member 110 is coupled to the upper member 130 by the intermediate layer 120. In one embodiment, the intermediate layer 120 directly bonds to the upper member 130 at the upper surface 125 of the upper portion 124 and the lower foot member 110 at the lower surface 126 of the lower portion 123. Alternatively, the intermediate layer 120 may be secured to the upper member 130 and/or the lower foot member 110 using a secondary bonding method. In one embodiment, the intermediate layer 120 is adhered to both the upper member 130 and lower foot member 110.

Depending on the chosen thicknesses 128 of the middle portion 127 of the intermediate layer 120, the upper member 130 will angle upward toward the heel portion 132 away from the lower foot member 110. As a result, the upper surface 135 of the upper member 130 at the mounting region 138 forms an acute angle with the plane 101, as shown in FIG. 2.

The foot prosthesis 100 further includes a mounting unit or block 140 that provides a means for connecting the foot prosthesis 100 to other prosthetic devices or components, such as a pylon, a socket or another suitable prosthetic component. The mounting unit 140 includes a fixed or removable coupler 141, such as a pyramid adapter or other suitable component, as is now known or later developed in the prosthetic industry. The mounting unit 140 also includes a mounting member 142 configured for attachment to the upper surface 135 of the upper member 130 at the mounting region 138. The mounting member 142 is generally about the same width 134 as the upper member 130, but may be narrower or wider, if desired. In one embodiment, the mounting member 142 includes a curved rearward end 143 and a curved forward end 144.

In one embodiment, the mounting unit 140 is formed from metal, including but not limited to stainless steel or titanium. In another embodiment, the coupler 141 may be formed from a composite material that is co-molded with the metallic mounting member 142 such that they are substantially integral. Alternatively, other materials having suitable properties, including but not limited to strength, durability and rigidity, may used for either or both of the mounting member 142 or coupler 141.

In order to provide the mounting unit 140 with a generally vertically oriented coupler 141, the mounting member 142 has a generally angled lower mounting surface 145 to mate with the angular configuration of the upper member 130 in the mounting region 138, as described above. The mounting unit 140 is positioned on the upper member 130 in the mounting region 138 with a center axis 103 of the coupler 141 generally aligned at about the rear side 129 of the middle portion 127 of the intermediate layer 120, as shown in FIG. 2.

The mounting member 142 is fixedly or removably attached to the upper member 130 using one or more attachment methods or means, as are known in the industry. In one embodiment, the mounting member 142 is adhered to the upper member 130 using an adhesive having suitable properties, as shown, for example, in FIG. 10 as adhesive layer 265. For example, the adhesive may include a polyurethane, an epoxy or a structural tape. In another embodiment, the mounting member 142 includes one or more mounting holes 177 that mate or align with through holes 139 in the mounting region 138 of the upper member 130. A retention member 160 including a corresponding number and size of threaded holes 161 is positioned against the lower surface 136 of the upper member 130 in the mounting region 138. One or more threaded fasteners 162, e.g., bolts, are then passed through the holes 177 and 139 into the threaded holes 161 and tightened down to attach the mounting member 142 to the upper member 130. As shown, three bolts 162 are used with two bolts of a first diameter and the third having a second, smaller diameter. In yet another embodiment, both an adhesive and the threaded fasteners are used for attachment. As stated previously, the upper portion 124 of the intermediate layer 120 can be shorter in length than the upper member 130 so that it does not extend between the retention member 160 and the lower surface 136 of the upper member 130. Thus, a more secure attachment of the mounting unit 140 may be achieved.

Other attachment methods and means, including but not limited to mechanical, chemical or other, may be used to attach the mounting unit 140 to the upper member 130. For example, the mechanical fasteners could pass through the retention member 160 and through the upper member 130 to thread into threaded holes in the mounting member 142. Alternatively, the fasteners could have an integral washer that eliminates the need for the retention member 160, or the fasteners could thread into threaded inserts that are bonded into the upper plate 130, with or without a retention member 160. Optionally, the mounting unit 140 may have a slot or cavity formed into the rearward end 143 to create a bonding surface for the upper member 130 and the upper member 130 could be adhered into the cavity, such as, for example, by potting as is known in the art.

The mounting member 142 also includes a forward portion 146 configured to project or cantilever over the upper surface 135 of the upper member 130. By projecting over the surface 135, the mounting member 142 provides a gap 147 between a lower surface 148 of the mounting member 142 and the upper surface 135 of the upper member 130. In one embodiment, the lower surface 148 has a convex curvature, however, other surface configurations may also be provided, including but not limited to straight or concave.

A resilient element 150, shown here having a generally wedge-like shape, is positioned within the gap 147 beneath the forward portion 146 in contact with the lower surface 148 and/or the upper surface 135. The resilient element 150 is generally compressible and elastic, such that the application of force or pressure by deflection of the upper member 130 and mounting member 142 toward each other results in compression and cushioning of the resilient element 150, yet allowing the upper plate 130 and mounting member 142 to return to their nominal positions relative to each other upon removal of the pressure. In one embodiment, the resilient element 150 is formed from the same material used for the intermediate layer 120. However, the resilient element 150 may be formed from a different material chosen, for example, from a list including but not limited to polymer foam, silicone rubber, butyl rubber, and natural rubber, all of which may be provided in different durometers that provide different degrees of compressibility, elasticity, etc., depending on the requirements of the prosthesis and the user. Alternatively, the resilient element 150 may be formed as one or more springs, such as a leaf spring, coil spring or other type of spring. The spring may be formed from a polymer, a metal or another suitable material.

In one embodiment, the resilient element 150 is bonded to the lower surface 148 but not to the upper member 130. A space 151 between the resilient element 150 and the upper member 130 may be a little as zero inches (zero millimeters), such that the resilient element 150 is in contact with the upper member or, alternatively, as much as about 0.1 inch (about 2.5 millimeters), such that the resilient element 150 is in close proximity to the upper member 130. In one embodiment, the space 151 ranges from about 0.01 inch to about 0.02 inch (about 0.25 millimeters to about 0.5 millimeters). Optionally, the resilient element 150 may be bonded to both the mounting member 142 and the upper member 130.

In another embodiment, the mounting member 142 may include one or more cavities adapted to receive one or more resilient elements 150 that may or may not includes protrusions or other structural features that interface with the cavities. For example, the mounting member 142 may include one or more slots or channels and the resilient element 150 may include one or more ridges adapted to be received within the slots. Optionally, the resilient element 150 may be formed integrally with the mounting member 142.

Figure 6:
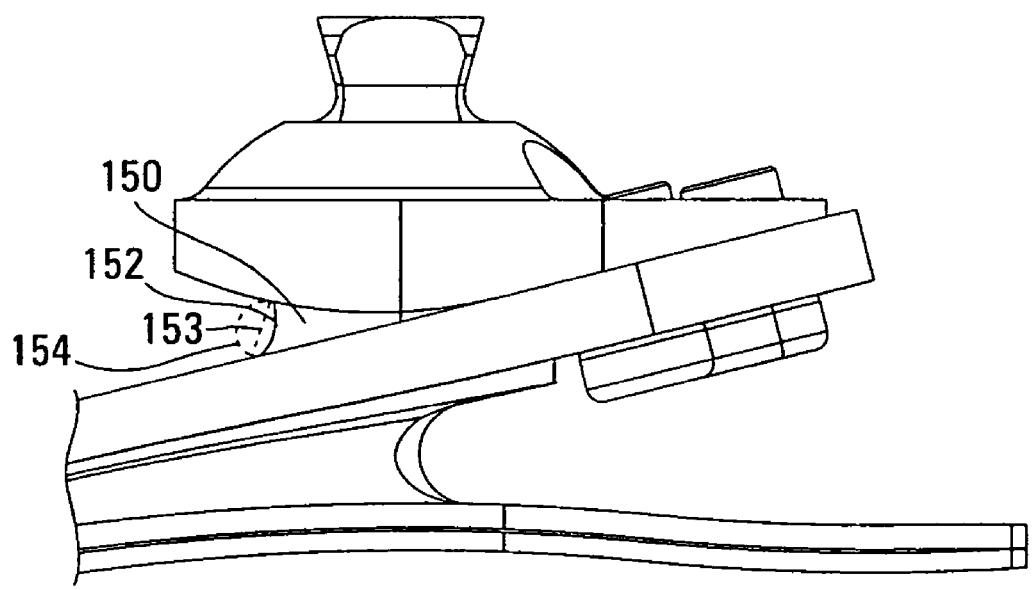
FIG. 6 is a partial side view of the foot prosthesis in accordance with the present invention showing an alternative embodiment of a resilient element.

The resilient element 150, as shown in FIG. 6, has a generally concave forward surface 152 that is generally transverse with respect to the upper member 130. Alternatively, a straight forward surface 153 that is angled generally toward the heel, the toe or vertically may be provided. Optionally, a convex forward surface 154 may be provided. In another embodiment shown in FIG. 7, a resilient element 172 includes a forward surface 173 that extends forward of the forward portion 146 of mounting member 142, which may or may not be provided as a covering layer on the upper surface 135 of the upper member 130. In addition, in this embodiment, the resilient element 172 does not extend rearward to generally fill the gap 147, as shown in prior embodiments. Instead, the resilient element 172 stops short, leaving a space 174 that may or may not be filled with a material.

Figure 8:
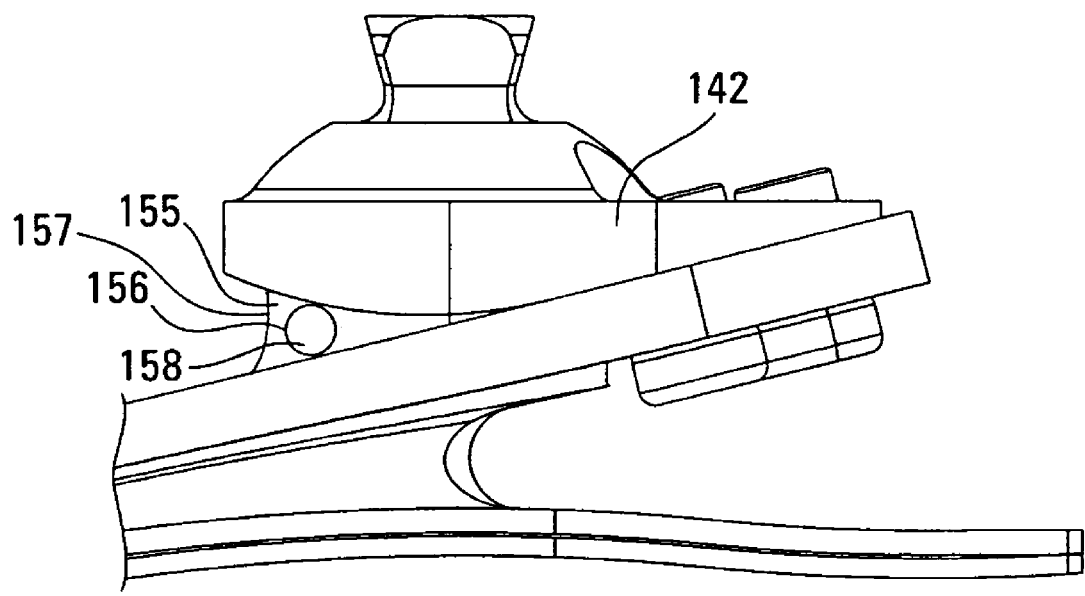
FIG. 8 is a partial side view of the foot prosthesis in accordance with the present invention showing an alternative embodiment of a resilient element.
Figure 9:
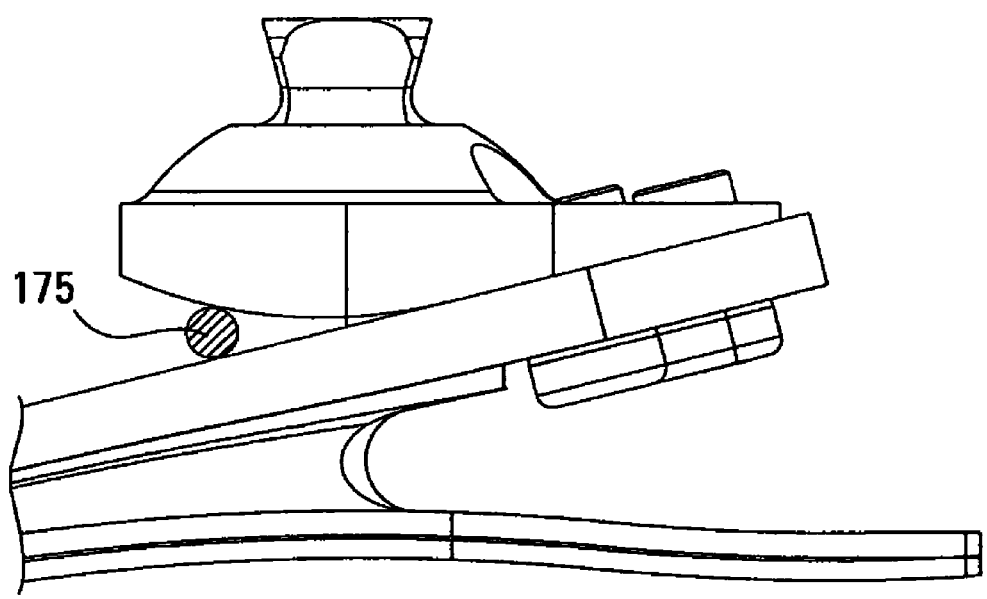
FIG. 9 is a partial side view of the foot prosthesis in accordance with the present invention showing an alternative embodiment of a resilient element.

The resilient element 150 may alternatively be configured to be removable, such that alternative resilient elements having different properties, such as, for example, material, size, durometer, and/or compressibility, may be interchanged to meet the requirements of the prosthesis 100 and the user. In another embodiment, shown in FIG. 8, a resilient element 155 includes a cavity or aperture 156, which may be a through hole, a blind hole from one side, two blind holes, one from each side, one or more cut outs in the forward surface 157, or other configurations that remove material and change the stiffness, resiliency and/or compressibility of the resilient element 155. In the embodiment shown, the cavity 156 is circular, however, other shapes and sizes may also be used. Optionally, one or more plugs 158 may be inserted into the cavity or cavities 156. The plug 158 may be formed of the same material as the resilient element 155 and have the same characteristics, the same material with different characteristics, or a different material, including but not limited to those described above, metal, polymer or other suitable materials. Alternatively, if a plurality of plugs 156 are provided, each plug 156 may have the same or different characteristics than each other plug 156. In yet another embodiment, shown in FIG. 9, a resilient element 175 may be simply shaped, such as, for example, a round rod as shown. However, other shapes, or rods having other cross-section shapes, may also be provided.

The resilient element 150 extends generally across a width 149 of the mounting member 142 and may conform to the curvature of the curved forward end 144. Alternatively, the resilient element 150 may extend only partially across the width 149 and may or may not be aligned with the longitudinal axis 102 of the prosthesis 100, as shown in FIG. 5. Optionally, the resilient element 150 may be provided in two or more parts, which may be aligned with, not aligned with and/or symmetrically or not symmetrically positioned with respect to the longitudinal axis 102.

Figure 10:
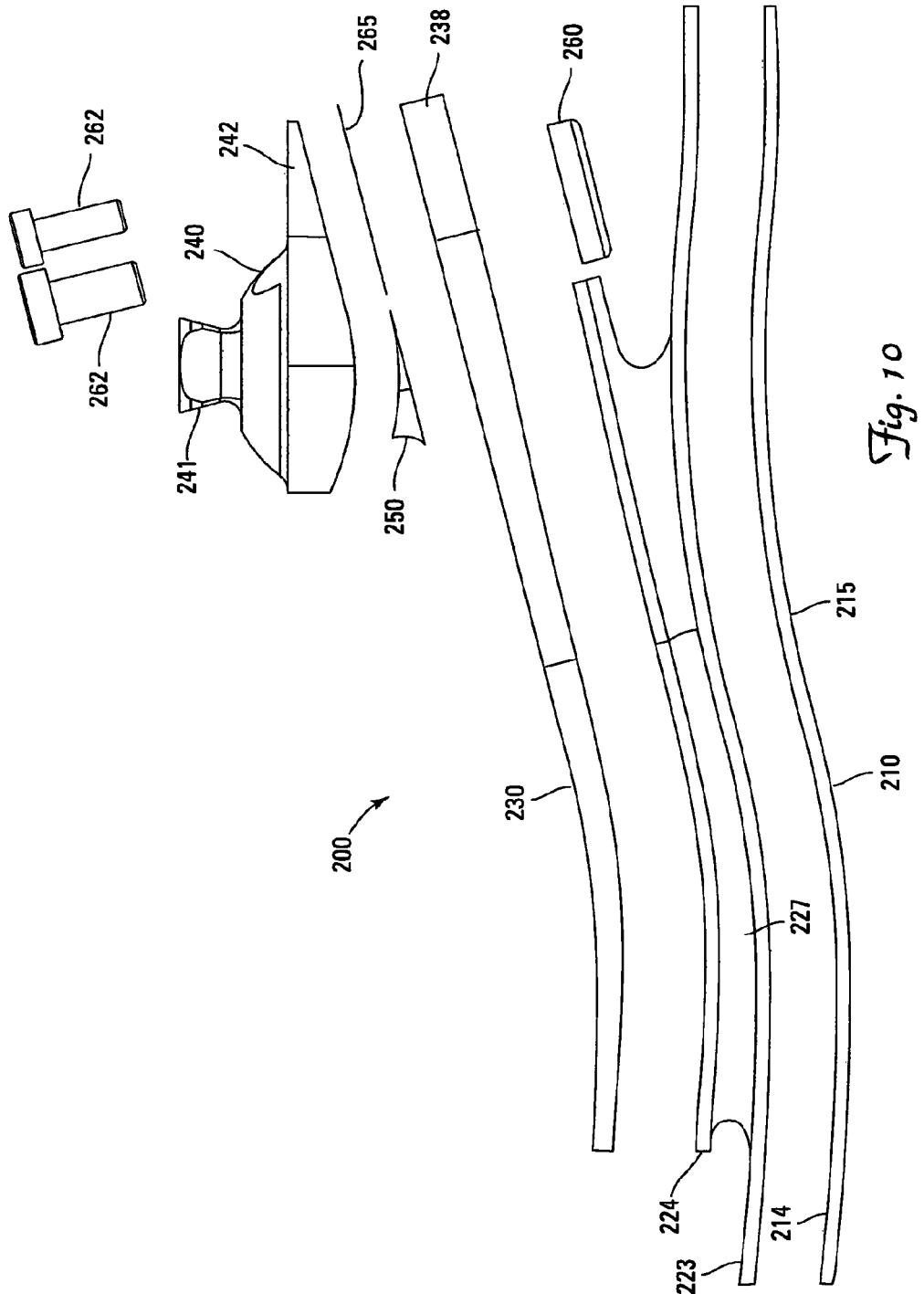
FIG. 10 is a side exploded view of a foot prosthesis in accordance with a second embodiment of the invention.

A second embodiment of a foot prosthesis 200 in accordance with the present invention is shown in FIG. 10 as an exploded assembly. This prosthesis 200 includes a lower foot member 210, an upper member 230 and an intermediate layer 220 interposed between the two, in a manner similar to the first embodiment. In this embodiment, however, the upper member 230 is chosen from the shorter length range described above with respect to the first embodiment, such that the lower foot member 210 has a length of about 8.6 inches up to about 10.3 inches (about 22 up to about 26 centimeters) and the upper member 230 has a length of about 6.4 inches (about 16.3 centimeters).

The intermediate layer 220 is also configured to correspond to the dimensions of both the upper member 230 and lower foot member 210. As a result, the relationship between the intermediate layer regions—lower portion 223, upper portion 224 and middle portion 227 —are the same as those described above.

In this embodiment, a mounting unit 240 also includes a generally vertical coupler 241 and is attached to a mounting region 238 of the upper member 230 at a mounting member 242. A retention member 260 and mounting fasteners 262 are similarly provided. Also included is a layer of adhesive 265 positioned in the mounting region 238 between the mounting member 242 and the upper member 230 as part of the attachment method, as described previously.

Figure 11:
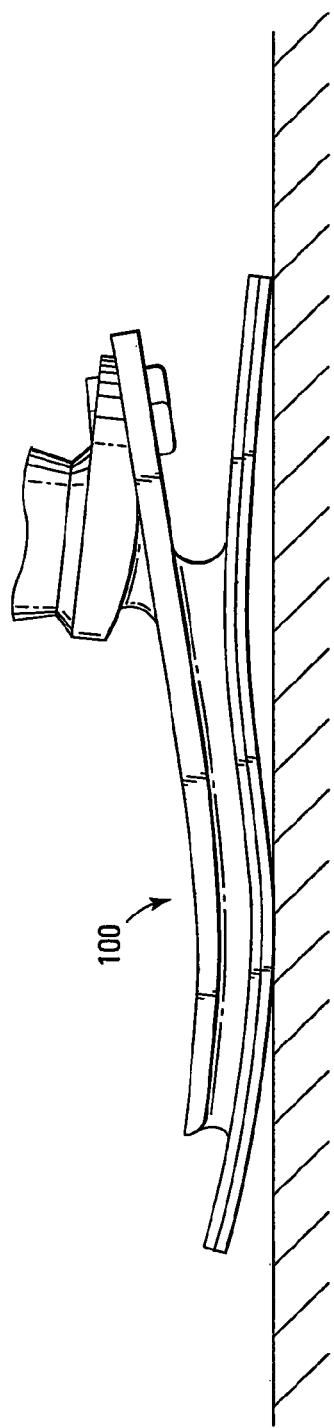

The foot prosthesis of the present invention is designed for greater stability during use, but with improved smoothness throughout rollover, that is, the transition from heel to toe. Referring to FIGS. 11-14, the foot prosthesis 100 of the first embodiment is shown during a normal gait cycle, such as when a user would take a step with the foot prosthesis 100. In FIG. 11, the prosthesis 100 is at rest with the weight of the user more evenly applied on a walking surface.

Figure 12:
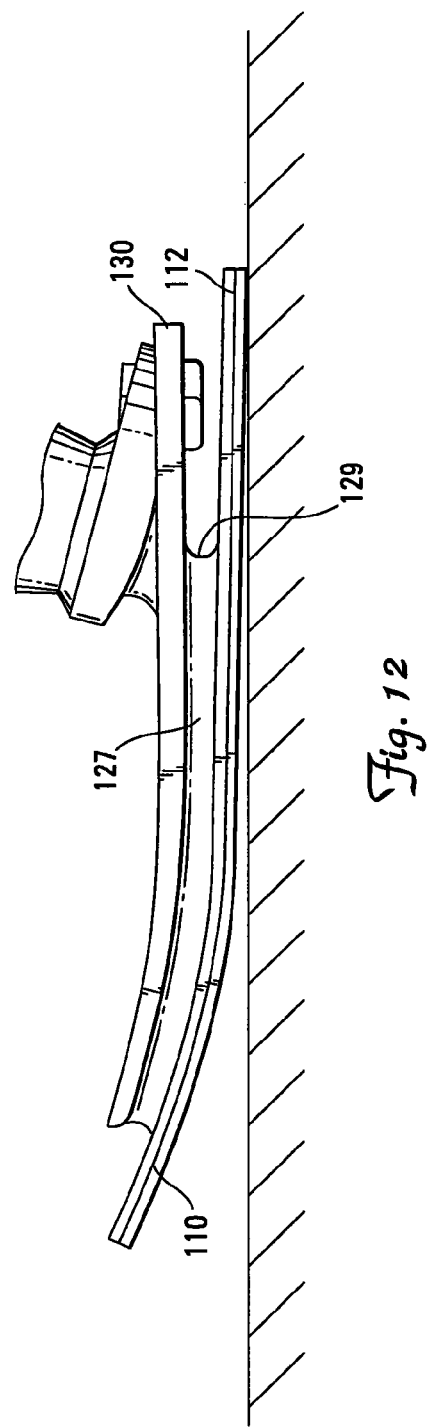

In FIG. 12, the user has stepped forward, placing weight at the heel, also known as heel strike. In this view, the heel portion 112 of the lower foot member 110 is deflected toward the upper member 130 and the intermediate layer 120 is compressed in the region of the rear side 129 of the intermediate middle portion 127. The heel portion 112, also known as a carbon activated heel, stores and returns energy put into it by the heel strike action.

In FIG. 13, the spring force of the deflected heel portion 112 propels the user's leg forward. In this view, the upper member 130 and lower foot member 110 flex in the mid regions 133, 113, respectively. The forward motion of the user's leg also causes the upper member 130 to move upward, compressing the resilient element 150. In action, the mounting unit 140 stays rigid while the upper member 130 and resilient element 150 react to the motion, such as be flexing, compressing, etc. As designed, the resilient element 150 becomes stiffer as it compresses, helping to make the transition from heel to toe more smooth and more like the performance and feel of a natural human foot and ankle.

In FIG. 14, the spring release of the mid foot propels the foot 100 forward to the toe portion 111 in a smooth transition. Compression of the resilient element 150 continues through toe-off and release of the force on the foot prosthesis 100. The lower foot member 110, the intermediate layer 120 and the upper member 130 flex, which also stores and returns energy during the end of the gait cycle.

In use, the configuration of the upper and lower members, 130, 110, in combination with the intermediate layer 120, define a spring whose spring rate is affected by the flexible and rigid portions of the upper member 130. By cantilevering the mounting member 142 over the upper member 130, a longer spring length in the upper member 130 is provided, which in turn enhances smoothness of the performance of the prosthesis 100. However, as the upper member 130 and mounting member 142 deflect relative to each other, stresses are created in the upper member 130 at the forward edge of the mounting region 138. By providing the resilient element 150 within the gap 147 formed by the cantilevered design, these stresses are dissipated and/or reduced within the upper member 130. As a result, a smoother performing, but more durable foot prosthesis 100 is provided. The resilient element 150 serves as a means to dissipate and/or spread out stress and to control deflection, and can be adjusted and/or optimized to meet the spring requirements of a particular user based on size, weight and/or activity level. The performance of the foot prosthesis of the present invention can be tailored by selecting the geometries and materials of one, or a combination, of the intermediate layer, the upper and lower foot members, the resilient element and the mounting unit.

As shown and described above, the intermediate layer 120, 220 is generally thinner than that used on many current prosthetic feet. The present invention's reduction of this material increases the strength and durability of the foot prosthesis. However, even in a reduced configuration, the intermediate layer 120, 220 in the present invention serves a number of purposes and is a means for coupling the upper member 130, 230 and lower foot member 110, 210 together. In addition, the configuration of the intermediate layer 120, 220 provides for some compression during use and serves as part of the spring formed by the foot prosthesis 100, 200. Further, the configuration provides for lateral and medial stability due to generally independent movement of the lower foot member 110, 210 with respect to the upper member 130, 230.

Figure 15:
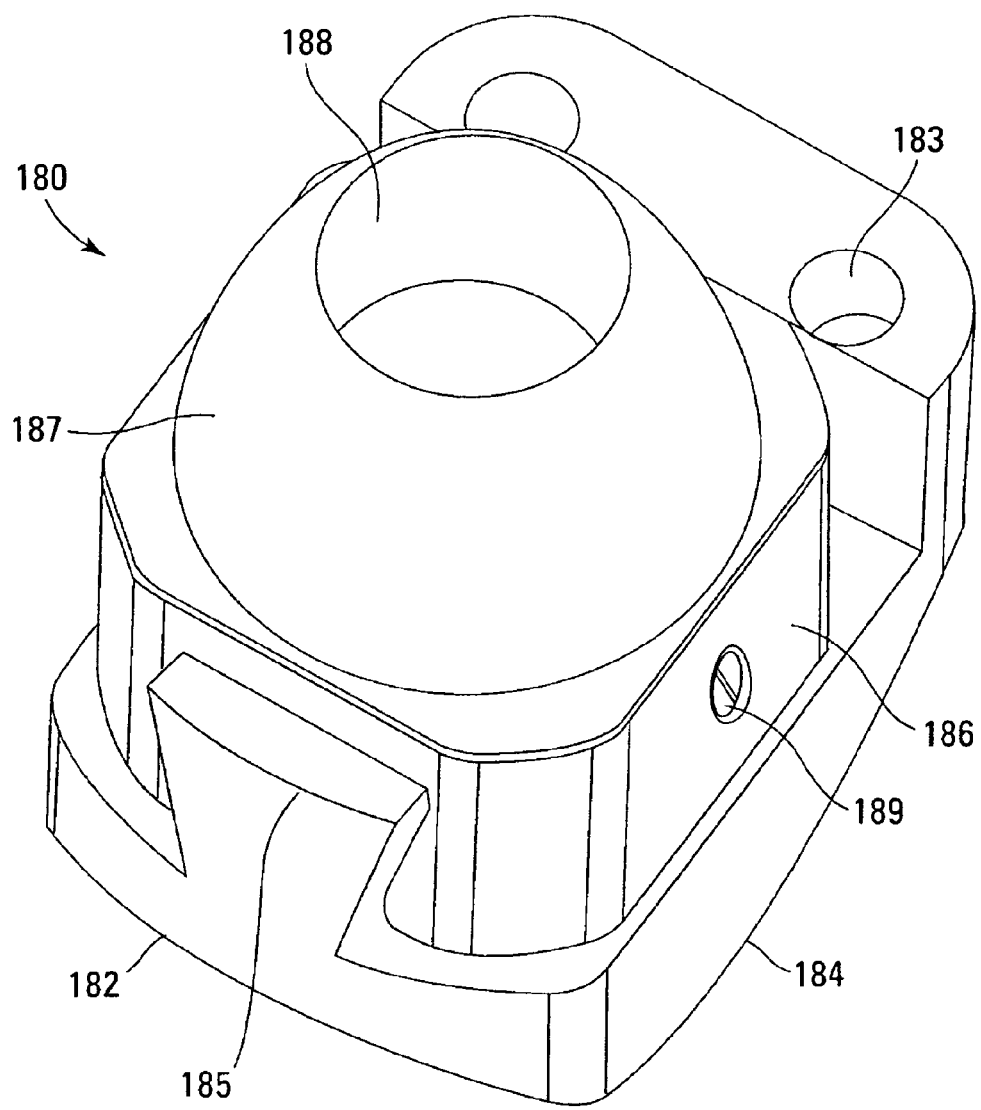
FIG. 15 is a perspective view of one embodiment of a mounting unit.
Figure 16:
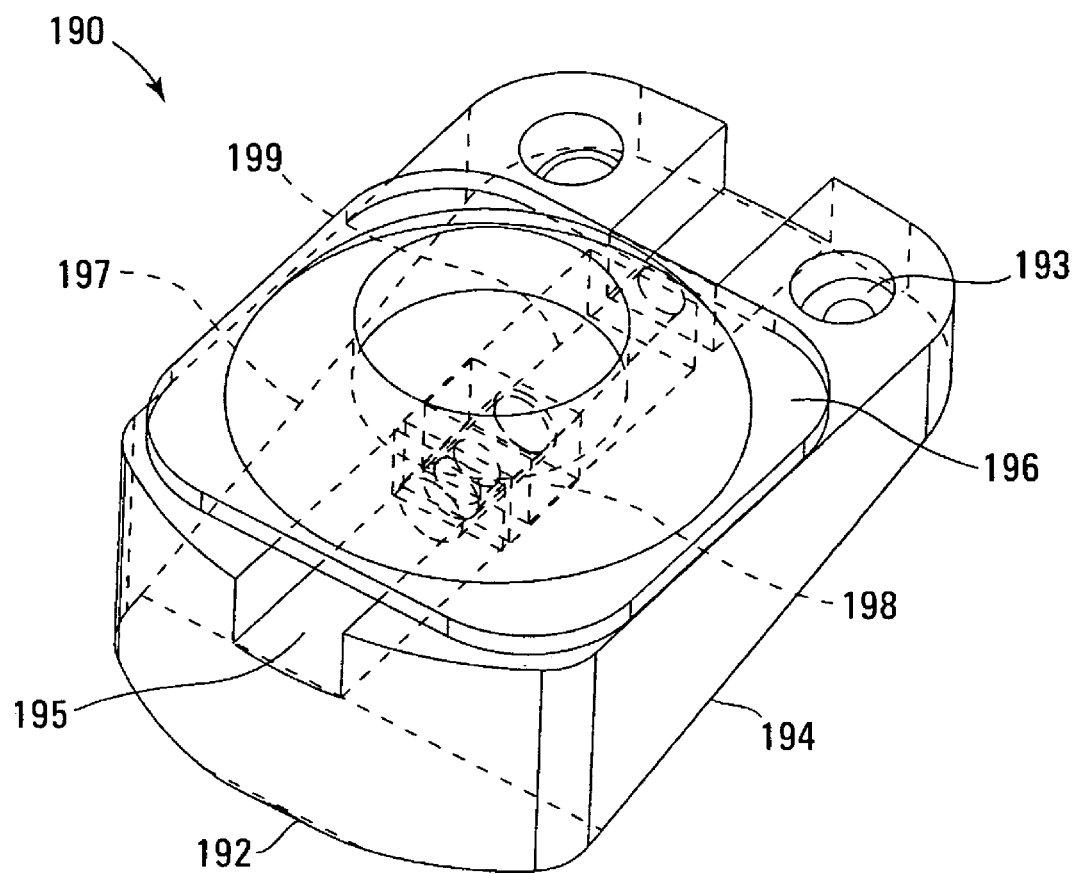
FIG. 16 is a perspective view of another embodiment of a mounting unit.

In FIGS. 15 and 16, additional alternative embodiments of a mounting unit 180, 190 are shown having a mounting member 182, 192 configured to be attached to an upper member of a foot prosthesis. In the first alternative embodiment 180, the mounting member 182 includes mounting holes 183 for receiving mechanical fasteners, such as bolts, to attach the mounting member 182 to another component, such as the upper member of the foot prosthesis. However, as described above, other attachment methods may be used. The mounting member 182 also includes a lower surface 184 that is configured to interface with the resilient element 150.

In this embodiment, the mounting member 182 is configured with a slide 185 upon which a coupler member 186 is slideably received. The slide 185 is shown having a generally trapezoidal cross-section to facilitate retention of the coupler member 186, however other cross-sections or configurations are also possible. The coupler member 186 includes a mounting dome 187 having an attachment opening 188. A coupling component, such as the pyramid adapter shown in the prior embodiments, may be attached to the coupler member 186 at the attachment opening 188 either in a fixed or removable manner. Other coupling components may alternatively be used. A set screw 189 or other suitable fastener may be provided to fix the coupler member 186 in a desired position, once it has been slideably adjusted along the slide 185. This adjustability allows for adjustment of the axis 103 of the coupler member 186, and thus the coupling component, which may prove useful in optimizing performance of the foot prosthesis for a particular user.

In the other embodiment 190, the mounting member 192 is configured with a channel 195 within which a coupler member 196 is slideably received. The channel 195 is shown having a generally rectangular cross-section to facilitate retention of the coupler member 196, however other cross-sections or configurations are also possible. The coupler member 196 also includes sliding unit 198 that is configured to ride within the channel 195 and is connected to a threaded member 199. The threaded member 199 is accessible from outside of the channel 195 for threadable adjustment of the sliding unit 198, such that rotation of the threaded member 199 results in the coupler member 196 sliding along the channel 195. The coupler member 196 also includes a mounting dome 197, similar to dome 187 and attachable to coupling components, as described above.

A number of mounting unit configurations have been shown and described above. Any of these configurations may be used in a foot prosthesis in accordance with the present invention. When removeably attached to an upper plate, any of the configurations may be interchanged with any other configuration, as needed to meet the needs of the user.

As described above, the middle portion 127 of the intermediate layer 120 may vary in thickness from a rear side 129 toward the toe portion 121 and may be as low as zero in some embodiments. For example, as shown in FIG. 17, the middle portion 127 may be configured with one or more openings or areas of zero material between the upper portion 124 and lower portion 123. Alternatively, as shown in FIG. 18, both the lower portion 123 and lower foot member 110 may also include an area of zero material in this area. Optionally, as shown in FIG. 19, the upper member 130 and lower foot member 110 may be substantially adjacent or in close proximity in this area.

Figure 20:
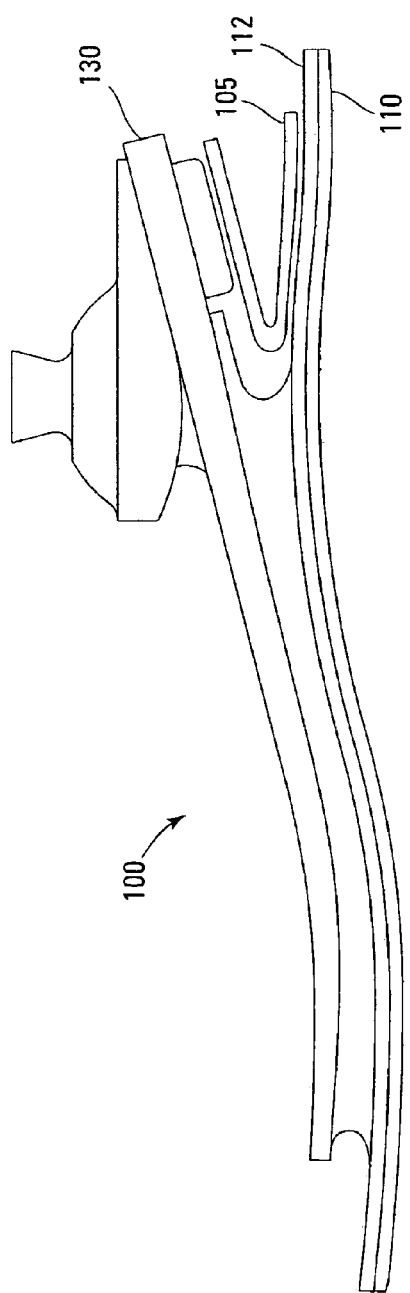
FIG. 20 is a side view of a foot prosthesis in accordance with the present invention including one embodiment of a heel spring member.
Figure 21:
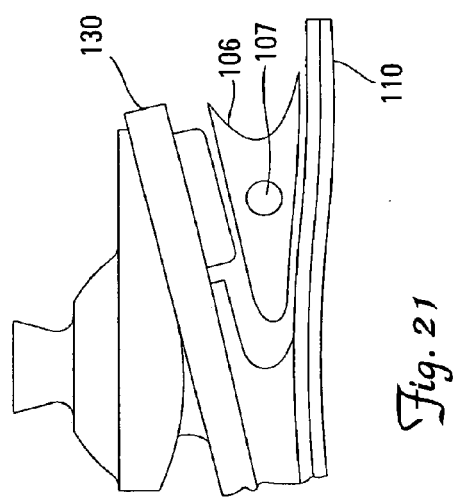
FIG. 21 is a partial side view of a foot prosthesis including another embodiment of a heel spring member.

In order to add further spring to the heel strike, the foot prosthesis 100 may also include additional spring-like components in the heel region. In FIG. 20, the foot prosthesis 100 includes a heel spring member 105 having a generally 'C-shaped' configuration. The heel spring member 105 is positioned between the upper member 130 and the lower foot member 110 at the rearward end 112 of the prosthesis 100. The heel spring member 105 may be formed from the same or similar resilient or compressible materials described above, such as polyurethane, or from a epoxy/carbon fiber material, or from a metal, polymer, or other suitable material. In FIG. 21, a heel spring member 106 includes a piece of resilient material that generally fills the space between the upper member 130 and the lower foot member 110. The heel spring member 106 may or may not include an opening 107 for modifying the stiffness of the member 106. In addition, the heel spring member 105, 106 may be removable and/or interchangeable so as to modify the performance of the foot prosthesis 100.

FIG. 22 shows a more light weight configuration of a foot prosthesis 300 configured with a single member 310 that includes a forward portion 315 and a rearward portion 320. The forward and rearward portions, 315, 320, are joined by a center curved portion 325 having a centerline 326 at the apex of the curved portion 325. A mounting unit 340 is attached to the member 310 forward of the centerline 326, in a manner similar to that described above for mounting units 140 and 240. A resilient element 350 is interposed between the mounting unit 340 and the member 310, also in a manner described above. In this embodiment, however, the foot prosthesis 300 does not include an upper member or an intermediate layer. Instead, the member 310 provides the necessary flexibility and smooth rollover in the transition from heel to toe, while providing an extremely light weight foot prosthesis 300. Alternatively, the mounting unit 340 may be positioned rearward of the centerline 326 (not shown). In FIG. 23, the foot prosthesis 300 is shown with the mounting unit 340 positioned at the apex of the curved portion 325, or generally aligned with the centerline 326. In this embodiment, the resilient element 351 may be provided as a disk having a contoured lower surface 352 or as an annulus or ring having little or no resilient material at the center of the resilient element 351.

FIGS. 24-45 provide alternative embodiments of the foot prosthesis of the present invention including mounting units and resilient elements. Each of the embodiments are described briefly below. Like terms as those used above will be used with respect to each embodiment.

In FIGS. 24-30, each embodiment includes a mounting unit cantilevered in a generally forward direction, or otherwise forming a gap toward the forward direction, toward the toe of the foot and attached to a member of the foot prosthesis at a rearward end of the mounting unit. As a result, the resilient element of each is interposed between the mounting unit and a foot member generally forward of the mounting unit's attachment location.

In FIGS. 31-38, on the other hand, each embodiment includes a mounting unit cantilevered in a generally rearward direction, or otherwise forming a gap toward the rearward direction, toward the heel of the foot, and attached to a member of the foot prosthesis at a forward end of the mounting unit. As a result, the resilient element of each is interposed between the mounting unit and a foot member generally rearward of the mounting unit's attachment location.

Figure 24:
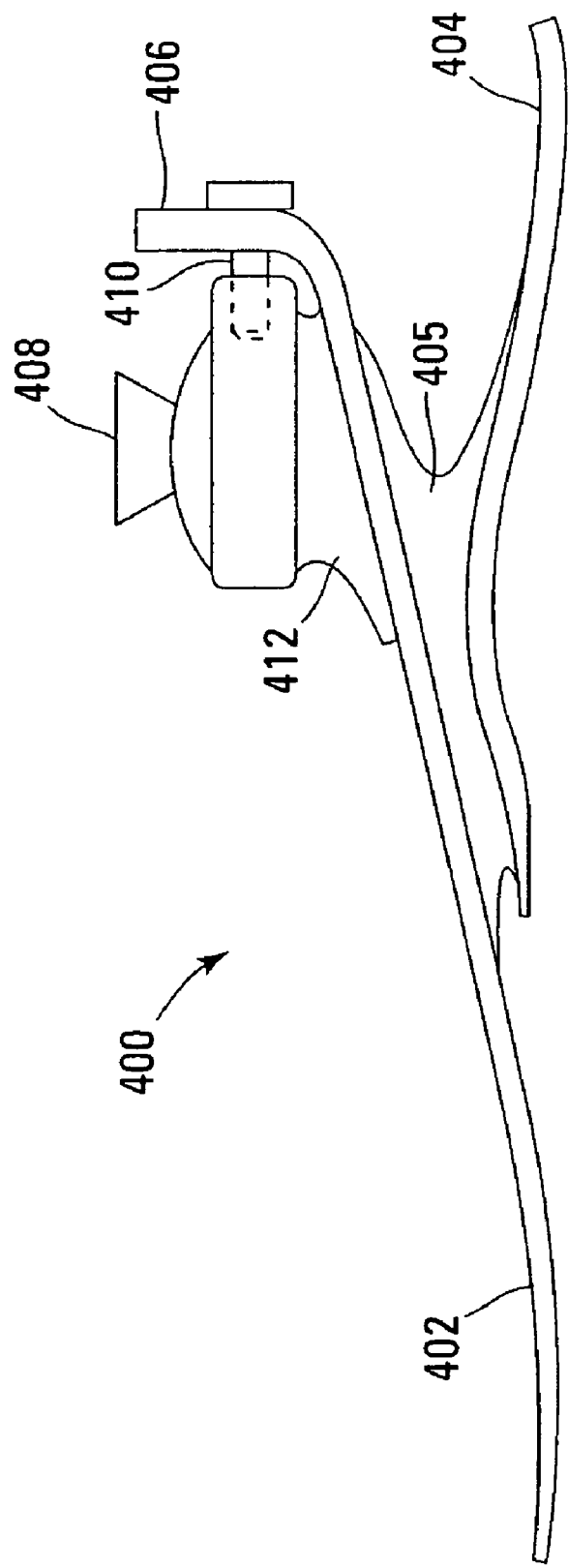

FIG. 24 shows a foot prosthesis 400 having an upper member 402 and a shorter lower heel member 404 attached to the upper member by a short intermediate layer 405. In this embodiment, the upper member 402 has a short upper extension 406 that extends generally upward away from the heel member 404. A mounting unit 408 is positioned above the upper member 402 and is attached at a rearward end 410 to the upper member 402 at the extension 406. A resilient element 412 is interposed between the mounting unit 408 and the upper member 402.

FIG. 25 shows a foot prosthesis 420 having an upper member 422 and generally 'C' shaped heel spring member 426 attached at a rearward end 425 of the upper member on a bottom side 423. A mounting unit 428 is positioned over a top side 424 of the upper member 422 and is fastened in a similar manner as described with respect to the first embodiment. A resilient element 430 is positioned between the mounting unit 428 and the top side 424 of the upper member 422.

FIG. 26 shows a foot prosthesis 440 similar to that shown in FIG. 2, with an upper member 442 coupled to a lower foot member 444 by an intermediate layer 443. In this embodiment, the upper member 442 curves upward with a rearward portion 446 extending farther away from the lower foot member 444. A mounting unit 448 is configured to attach to this curved rearward portion 446 of the upper member 442 and a resilient element 450 is interposed and positioned between the upper member 442 and the mounting unit 448.

FIG. 27 shows a foot prosthesis 460 similar to foot prosthesis 440 shown in FIG. 25, but in this embodiment the lower foot member 464 is a shorter heel member coupled to the upper member 462 by a shorter intermediate layer 465.

Figure 28:
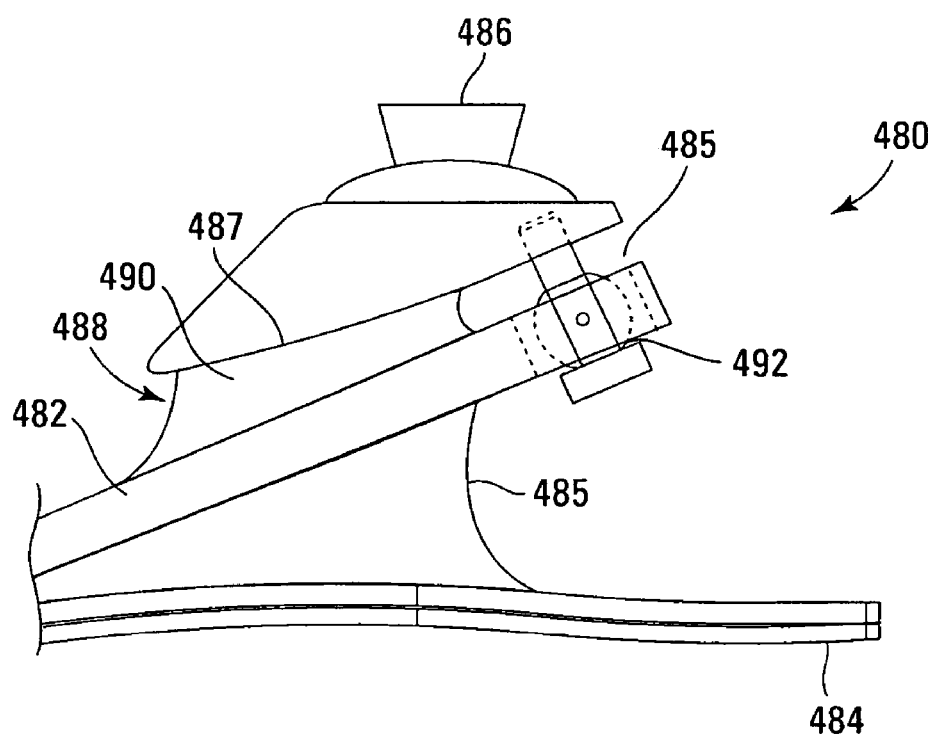

FIG. 28 shows a detailed view of a rearward portion of a foot prosthesis 480 having an upper member 482 coupled to a lower foot member 484 by an intermediate layer 485. A mounting unit 486 is attached to the upper member 482 at a rearward end 485. In this embodiment, the mounting unit 486 has an elongated lower surface 487 providing a greater area of gap 488 between the mounting unit 486 and upper member 482. More volume of a resilient element 490 is shown interposed and positioned between the mounting unit 486 and upper member 482. The mounting unit 486 is shown attached using a fastener and/or bearing 492, but other attachment methods and means are also usable.

Figure 29:
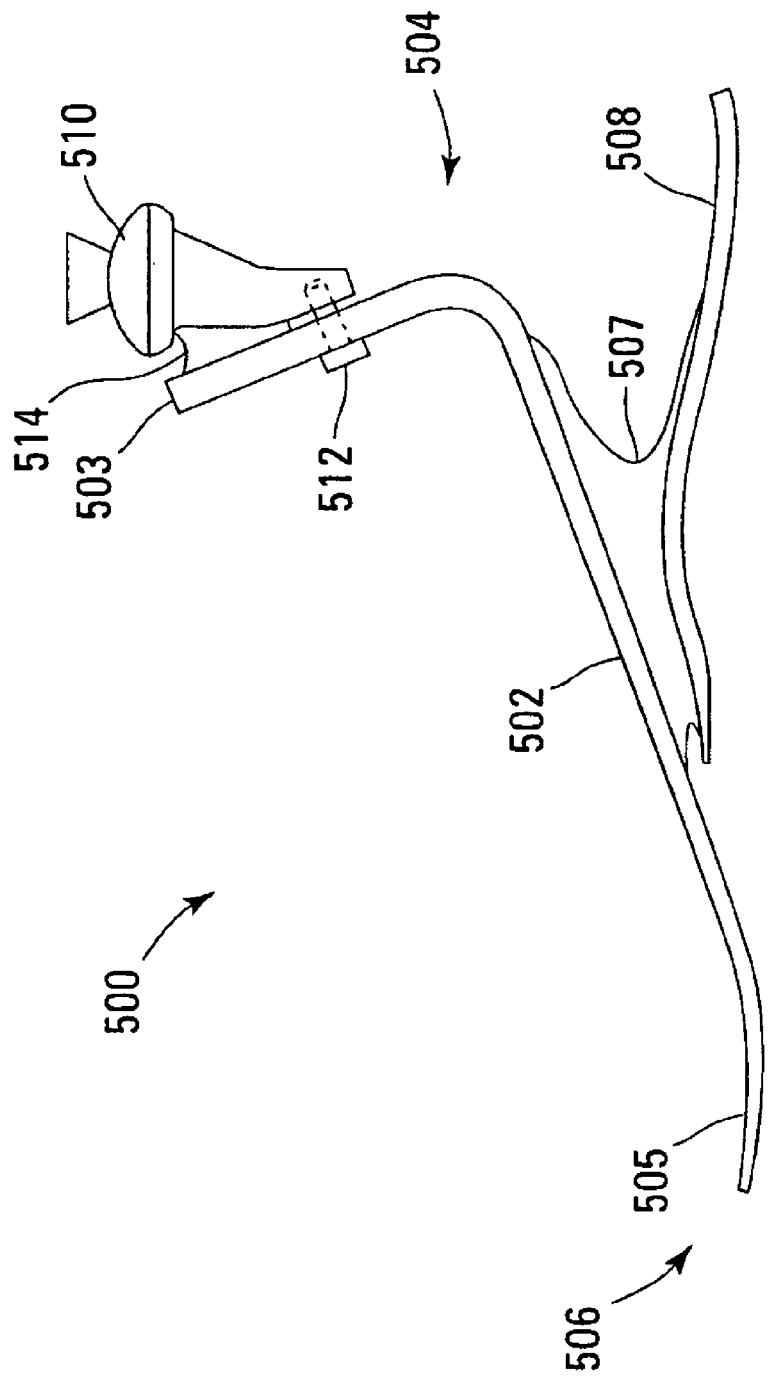

FIG. 29 shows a foot prosthesis 500 including an upper member 502 having an extension 503 at a rearward end 504 and a lower part 505 at a forward end 506. A shortened lower member 508 is coupled to the upper member 502 by an intermediate layer 507 and serves as a heel portion, however a full length lower member coupled by an appropriately size intermediate layer is also possible. The extension 503 extends generally upward, away from the lower member 506 at about a right angle to the lower part 505 of the upper member 502 and thus is angled generally toward the forward end 506. The extension 503 includes a forward surface 508 and a rearward surface 509. A mounting unit 510 is coupled to the rearward surface 509 of extension 503 at a lower end 511 by a fastener and/or a bearing 512 and is configured to be generally vertical. A resilient element 514 is interposed between the mounting unit 510 and the upper member extension 503.

Figure 30:
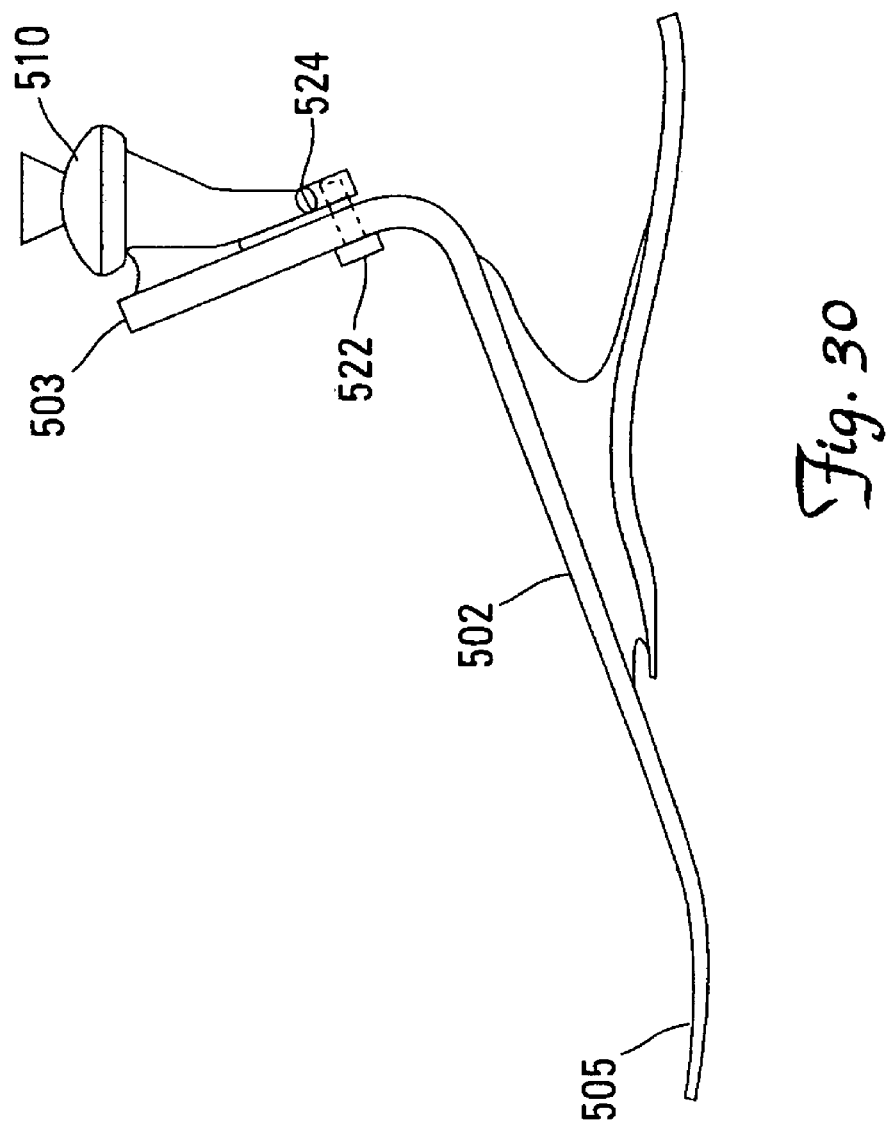

FIG. 30 shows a foot prosthesis 520 similar to foot prosthesis 500 shown in FIG. 28, but in this embodiment the mounting unit 510 couples to the upper member extension 503 by a fastener 522 at a hinged portion 524.

Figure 31:
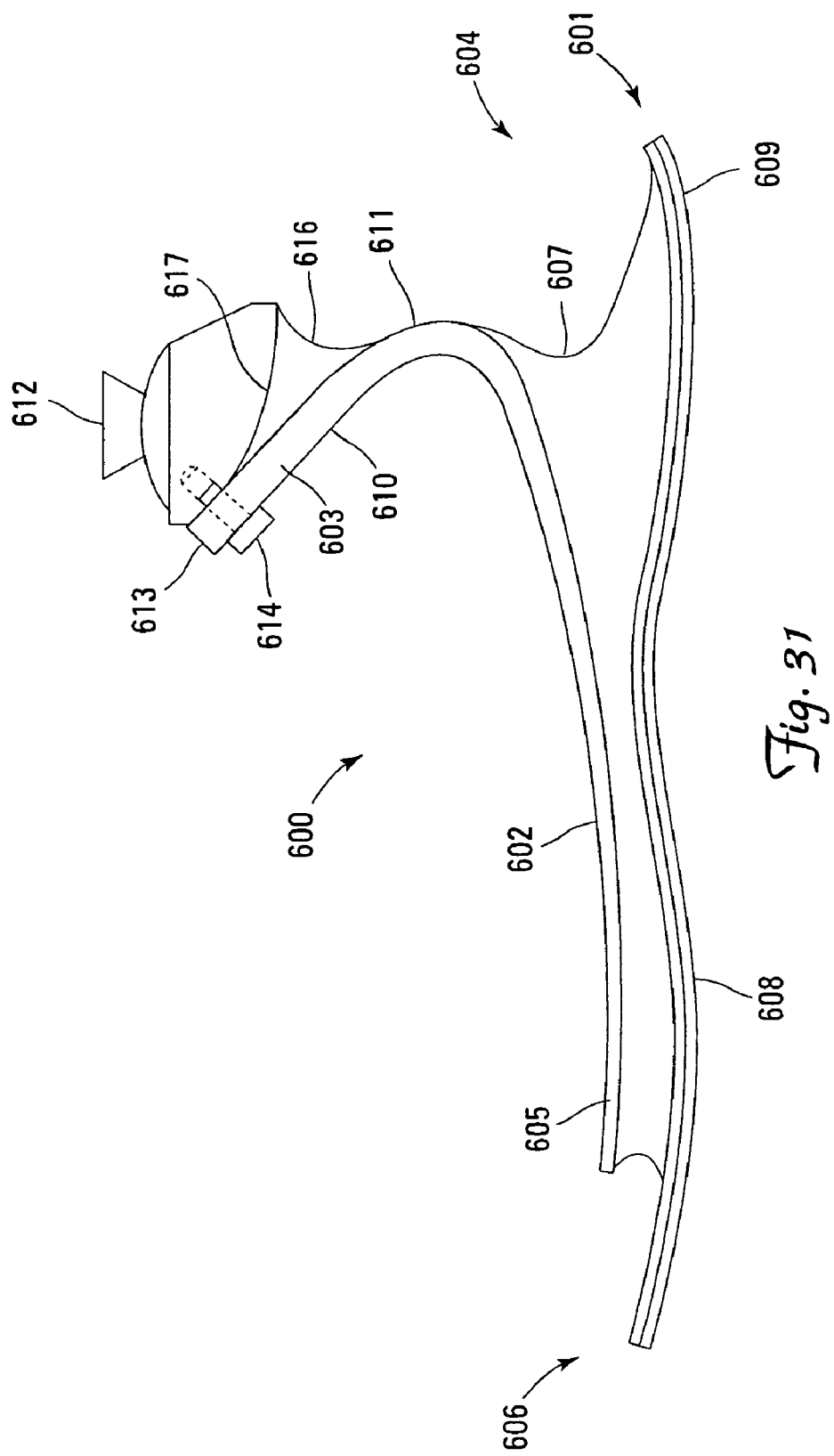

FIG. 31 shows a foot prosthesis 600 similar to FIG. 28, including an upper member 602 having an extension 603 at a rearward end 604 and a lower part 605 at a forward end 606. In this embodiment, a lower foot member 608 is a full length member coupled to the upper member 602 by an intermediate layer 607, and includes a heel portion 609. However, a shorter, heel portion lower foot member, such as that shown in FIG. 31, may also be provided. The extension 603 extends generally upward, away from the lower member 608 at about a right angle to the lower part 605 of the upper member 602 and thus is generally angled toward the forward end 606. The extension 603 includes a forward surface 610 and a rearward surface 611. In this embodiment, a mounting unit 612 is attached to the rearward surface 611 of the extension 603 at an upper end 613 by a fastener 614, and is cantilevered toward a rearward end 601 of the foot prosthesis 600. A resilient element 616 is interposed between a lower surface 617 of the mounting unit 612 and the rearward surface 611 of the extension 603.

Figure 32:
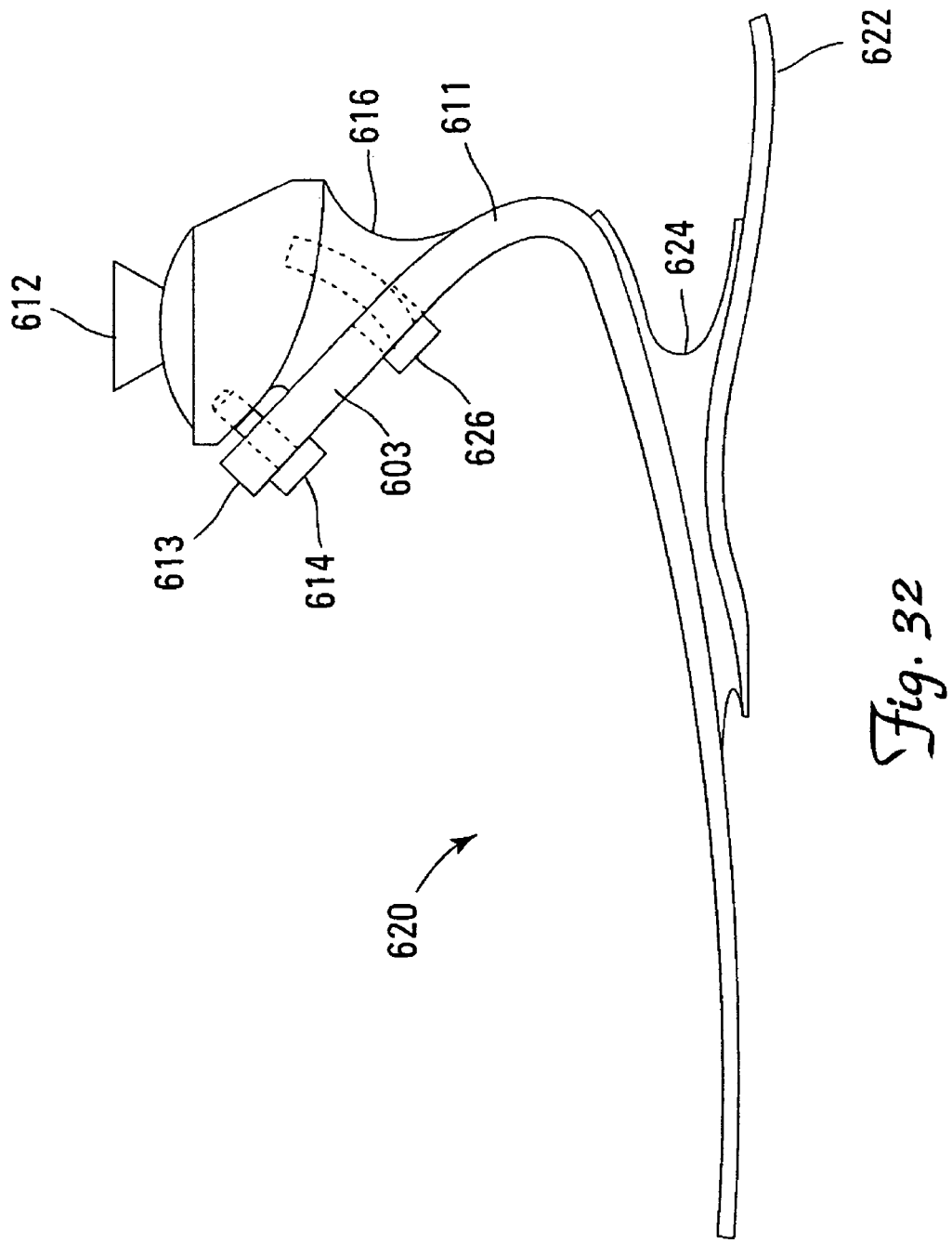

FIG. 32 shows a foot prosthesis 620 similar to FIG. 30. In this embodiment, however, the full length lower foot member 608 is replaced by a shorter heel portion lower foot member 622 that is coupled to the upper member 602 by an appropriately sized intermediate layer 624. Also in this embodiment, the mounting unit 612 is attached to the upper member extension 603 by multiple fasteners 614, at least one of which 626 passes through the resilient element 616.

Figure 33:
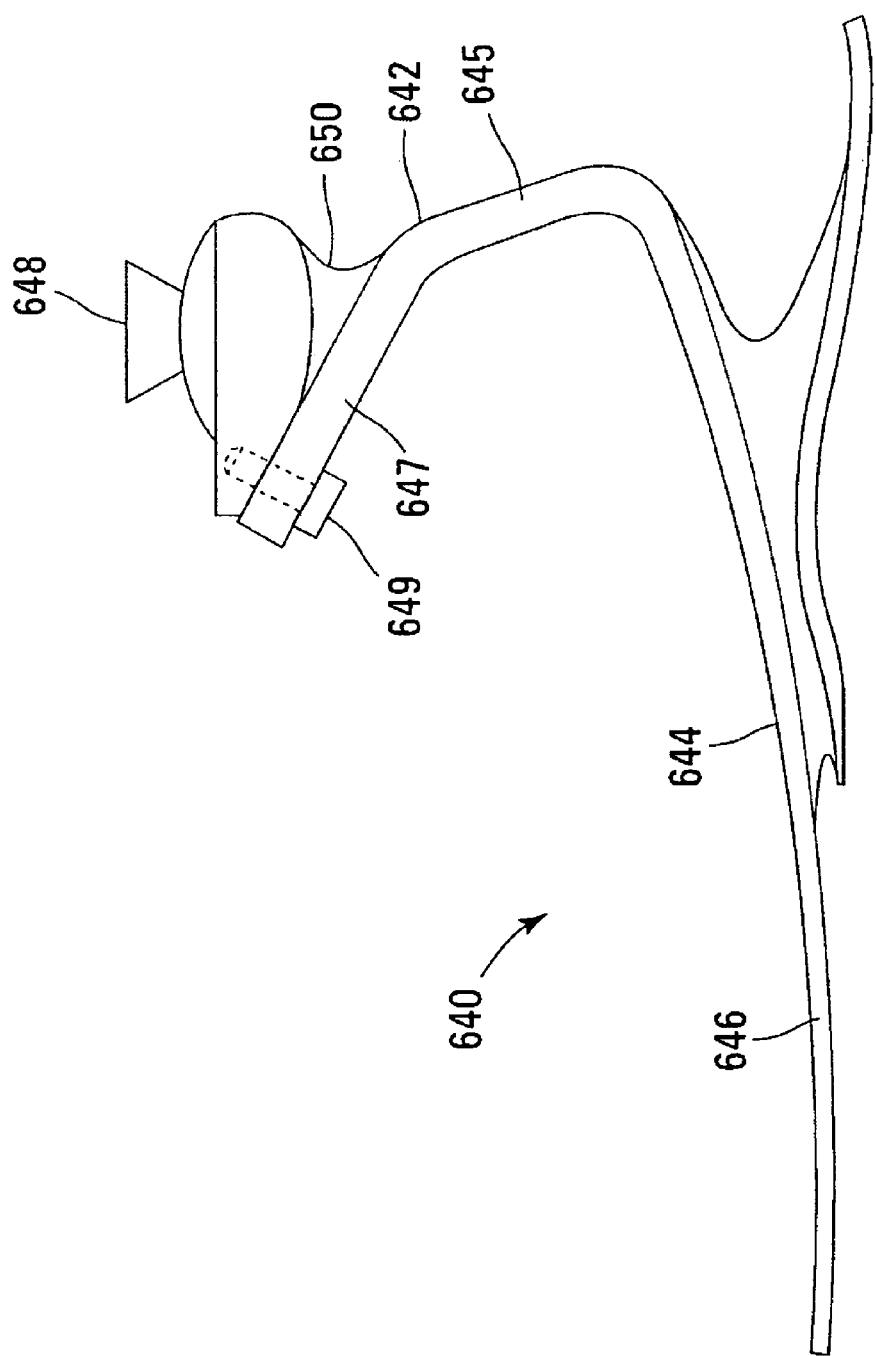

FIG. 33 shows a foot prosthesis 640 similar to those shown in FIGS. 30 and 31, but in this embodiment the extended portion 642 of the upper member 644 includes a generally straight portion 645 positioned between a lower portion 646 and angled forward upper portion 647. A mounting unit 648 is attached to the angled upper portion 647 using fasteners and/or bearings 649 and a resilient element 650 is positioned generally under the mounting unit 648 between the mounting unit 648 and the angle upper portion 647.

FIG. 34 shows a foot prosthesis 660 similar to prosthesis 600 shown in FIG. 30. However, in this embodiment, the lower surface 662 of the mounting member 664 is configured differently to be generally convex. As a result, the resilient element 666 also has a different configuration to correspond to the mounting unit 664. The mounting unit 664 is attached by the fastener 614.

FIG. 35 shows a detailed view of a heel portion 670 of a lower foot member 672 of a foot prosthesis, such as those shown above. In this embodiment, the lower foot member 672 is coupled to an upper member 674 by an intermediate layer 676. The intermediate layer 676 includes an upper portion 677 positioned adjacent the upper member 674 and a lower portion 678 positioned adjacent to the lower foot member 672. In some embodiments shown herein, the lower portion 678 of the intermediate layer 676 extends substantially to a rearward end 671 of the lower foot member 672. In this embodiment, the lower portion 678 does not extend all the way to the rearward end 671 of the lower foot member 672. This variation of the intermediate layer 676 may affect the spring properties of the heel portion 670.

FIG. 36 shows a detailed view of a mounting unit 680 attached to an upper member 682 with a resilient element 688 positioned between the mounting unit 680 and the upper member 682. The mounting unit 680 is attached by a fastener and/or bearing 684.

FIG. 37 shows another detailed view of the mounting unit 680 attached to the upper member 682. In this embodiment, the mounting unit is attached by multiple fasteners or bearings 684, but with at least one fastener or bearing 686 passing through the resilient element 688.

FIG. 38 shows a foot prosthesis 690 similar to that shown in FIG. 31, but in this embodiment a backward 'L' shaped second upper member 692 is coupled to the first upper member 693 on a first surface 694 away from the lower member 695. A second intermediate layer 696 is provided between the lower leg 697 of the 'L' member 692 and the first surface 694 of the first upper member 693 and above the first intermediate layer 698. The second end of the 'L' member 699 is positioned adjacent to the extended portion 691 of the first upper member 693.

FIGS. 39-42 show a foot prosthesis 700 similar to that shown in FIG. 29, but with a full length lower foot member 702. In FIG. 39, the upper member 704 extends upward away from the lower foot member 702 and angles forward over the upper member 704 at portion 705, similar to extension 503. In this embodiment, however, the upper member 704 then angles back so as to provide a substantially vertical portion 706 of the upper member 704. A generally vertical mounting unit 708 is attached to the vertical portion 706 of the upper member 704 forming a gap between the mounting unit 708 and the upper member 704, with a resilient element 709 positioned within the gap between the mounting unit 708 and upper member 704.

FIG. 40 shows a second variation for attaching a generally vertical mounting unit 710 to the vertical portion 706 of the upper member 704. A resilient element 711 is positioned between the mounting unit 710 and the vertical portion 706. FIG. 41 shows a third variation for attaching a generally vertical mounting unit 712 to the vertical portion 706 of the upper member 704. A resilient element 713 is positioned between the mounting unit 712 and the vertical portion 706. FIG. 42 shows a fourth variation for attaching a generally vertical mounting unit 714 to the vertical portion 706 of the upper member 704. A resilient element 715 is positioned between the mounting unit 714 and the vertical portion 706.

Figure 43:
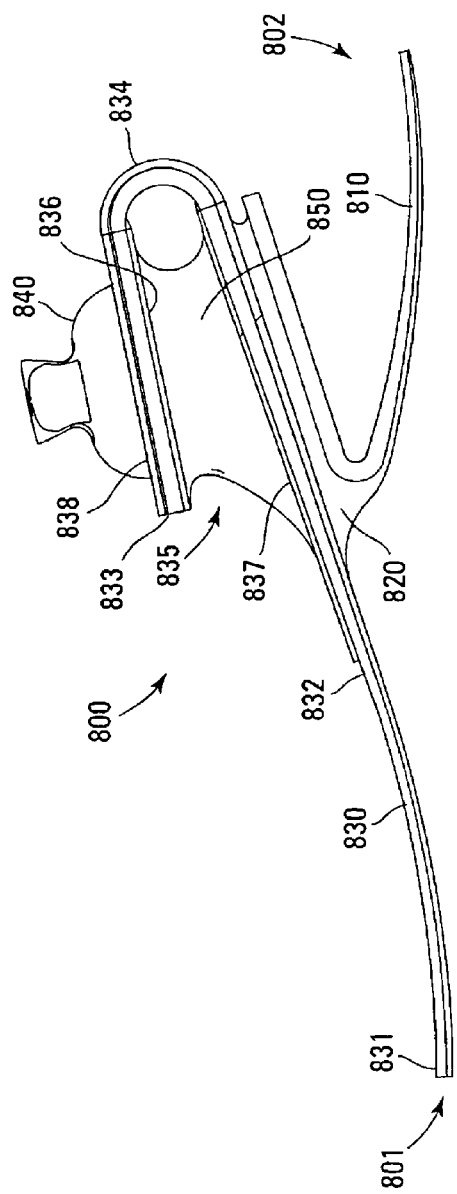

In FIG. 43, another embodiment of a foot prosthesis 800 is shown having a lower member or plate 810, an upper member or plate 830 and an intermediate layer 820 coupling the two together. The upper member 830 includes a first end 831 generally positioned at a forward toe region 801 of the foot prosthesis 800, a middle region 832 and a second end 833. The middle region 832 is connected to the second end 833 by a bend 834. The bend 834 in the upper member 830 results in the second end 833 wrapping over the middle region 832 to some extent, such that the second end 833 is directed toward the forward region 801. The wrapping of the second end 833 creates a gap 835 between a bottom surface 836 of the second end 833 and a top surface 837 of the middle region 832. In this embodiment, the lower member 810 is formed as a generally 'C' shaped spring element that provides a heel region 802 for the foot prosthesis 800.

The foot prosthesis also includes a mounting unit or block 840 that is attached to the upper member 830 on a top surface 838 of the second end 833 in a manner similar to those described above. In this embodiment, a resilient element 850 is interposed within the gap 835 between the second end 833 and the middle region 832, as opposed to a gap between the mounting unit and the upper member as described in the embodiments above. The resilient element 850 may be configured and attached in one or more of the ways described above, but in generally does not usually fill the gap 835 in a region adjacent to the bend 834.

Figure 44:
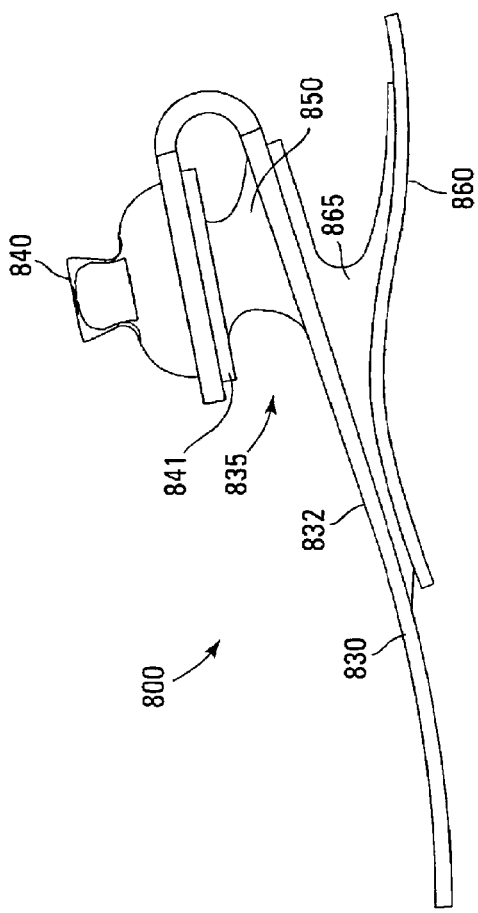

In FIG. 44, an alternate embodiment of the foot prosthesis 800 is shown having upper member 830 and mounting unit 840. In this embodiment, however, lower member 860 is configured as a curved plate and intermediate layer 865 couples the lower member 860 to upper member 830 while providing a resilient spring. Resilient element 850 is provided within the gap 835, but in this embodiment, a mounting plate 841 is interposed between the resilient element 850 and the lower surface 836 of the second end 833. The mounting plate 841 is then used to secure the mounting unit 840 to the second end 833.

In FIG. 45, another alternate embodiment of the foot prosthesis 800 is shown having upper member 830, lower member 810, mounting unit 840 and resilient member 850. In this embodiment, however, a third member or plate 880 is provided at the toe region 801. The third member 880 is coupled to the upper member 830 by a second intermediate layer 885. Both the lower member 810 and third member 880 are configured to engage a walking surface. Thus, the upper member 830 does not engage a walking surface.

Although the invention has been described in detail with reference to the presently preferred embodiments, those of ordinary skill in the art will appreciate that various modifications can be made without departing from the invention. As one example, each of the features in each of the above-described embodiments could, in many cases, be combined with one or more features of another of the embodiments. Also, though components or portions of the above-described embodiments are described in some cases in terms of anatomical components or portions, this is not meant to imply that such embodiment components or portions provide any or all of the performance provided by the anatomical components or portions (e.g., toe portion and a toe).

We claim:

1. A foot prosthesis having improved rollover and stability comprising:
   a first plate having a toe region at a forward end, a heel region at a rearward end, a lower surface and an upper surface, wherein the upper surface angles upwardly toward the rearward end;
   a second plate having a toe region at a forward end, a heel region at a rearward end, an upper surface which is coupled to the lower surface of the first plate and a lower surface which is configured to engage a walking surface;
   a resilient intermediate member interposed between and coupled to the first and second plates at a location anterior to the heel region of the first plate;
   a mounting unit having a coupler configured to be coupled to a user of the foot prosthesis and a mounting portion, the mounting portion including a non-planar lower surface, the non-planar lower surface including a mounting surface at a first end of the mounting unit that contacts and is fixed to the upper surface of the first plate, and a projection surface at an opposite second end of the mounting unit extending forwardly from the mounting surface such that a gap is defined between the projection surface and the upper surface of the first plate, the projection surface being movable toward and away from the upper surface of the first plate; and
   a resilient element positioned at least partially within the gap between the projection surface and the upper surface of the first plate, the resilient element comprising a compressible material configured to dissipate stress in the first plate and control deflection between the first plate and the mounting unit.

2. The foot prosthesis of claim 1, wherein the intermediate member is bonded to the first plate at the toe region.

3. The foot prosthesis of claim 1, wherein the mounting unit is substantially rigid and the first plate is at least partially flexible.

4. The foot prosthesis of claim 1, wherein the resilient element comprises a wedge or a rod.

5. The foot prosthesis of claim 1, wherein the resilient element substantially fills the majority of the gap.

6. The foot prosthesis of claim 1, wherein the resilient element is interchangeable.

7. The foot prosthesis of claim 1, wherein the resilient element comprises a front surface extending generally transversely across the first plate, wherein the front surface is one of convex, concave and planar.

8. The foot prosthesis of claim 1, wherein the non-planar lower surface of the mounting portion comprises a longitudinally curved surface.

9. The foot prosthesis of claim 1, wherein the mounting unit is fastened to the first plate.

10. The foot prosthesis of claim 1, wherein the mounting unit is rigid and the first plate is substantially rigid when attached to the mounting unit.

11. The foot prosthesis of claim 1, wherein the first plate is angled relative to an upper surface of the coupler.

12. The foot prosthesis of claim 1, wherein the toe and heel regions of the second plate are connected by a bend.

13. The foot prosthesis of claim 12, wherein the heel region of the second plate includes a heel portion.

14. A foot prosthesis comprising:
   a first plate having a toe region and upper and lower surfaces;
   a second plate having a toe portion and a heel portion, which is coupled to the first plate such that the lower surface of the first plate is spaced apart from an upper surface of the second plate;
   a resilient intermediate member interposed between and coupled to the first and second plates, wherein the resilient intermediate member is coupled to the first plate at or near the toe region of the first plate;
   a mounting unit having a coupler configured to be coupled to a residual limb interface of a user, and a mounting portion, the mounting portion including an angled mounting surface contacting and fixed relative to the upper surface of the first plate at a first end of the mounting unit, and a projection portion positioned at an opposite end of the mounting unit and extending forwardly from the mounting surface toward the toe region with a gap defined between the projection portion and the upper surface of the first plate, the projection portion being moveable toward and away from the upper surface of the first plate; and
   a resilient element positioned at least partially within the gap, the resilient element comprising a polymer material configured to dissipate stress in the first plate and control deflection between the first plate and the mounting unit.

15. The foot prosthesis of claim 14, wherein the first plate is at least partially flexible, and the mounting unit is rigid and wherein a portion of the first plate that is connected to the first end of the mounting unit is substantially rigid when attached to the mounting unit.

16. The foot prosthesis of claim 14, wherein the resilient element is removable.

17. The foot prosthesis of claim 14, wherein the first plate is angled relative to the upper surface of the second plate.

18. A foot prosthesis comprising:
- a first plate having a toe region, a heel region, an upper surface, and a lower surface;
- a second plate having a toe region, a heel region, an upper surface and a lower surface, the upper surface of the second plate being coupled to the lower surface of the first plate, and the lower surface being configured to contact a walking surface;
- a mounting unit having a coupler configured to connect a foot prosthesis to a residual limb interface of a user, and a mounting portion including a mounting surface, the mounting surface having a first end portion that is fixed to the upper surface of the first plate, and a second end portion that is moveable toward and away from the upper surface of the first plate;
- a resilient element positioned between the second end portion of the mounting surface and the upper surface of the first plate;
- wherein the mounting surface of the mounting unit is contoured with the second end portion of the mounting surface curving away from the upper surface of the first plate.

19. The foot prosthesis of claim 18, further comprising a resilient intermediate member interposed between the first and second plates at the toe region of the first plate.

20. The foot prosthesis of claim 18, wherein the mounting unit is connected to the first plate with a fastener that is positioned at the first end portion of the mounting surface.

21. The foot prosthesis of claim 18, wherein the first end portion of the mounting surface is positioned on a toe side of the coupler toward the toe region of the first plate, and the second end portion of the mounting surface is positioned on a heel side of the coupler toward a heel region of the first plate.

* * * * *